(12) United States Patent
Vaeck et al.

(10) Patent No.: US 6,335,008 B1
(45) Date of Patent: Jan. 1, 2002

(54) HYBRID GENES INCORPORATING A DNA FRAGMENT CONTAINING AT LEAST ONE GENE ENCODING AN INSECTICIDAL PROTEIN AND A GENE ENCODING A GLUTAMINE SYNTHASE INHIBITOR, PLASMIDS, TRANSFORMED CYANOBACTERIA EXPRESSING SUCH PROTEINS AND METHOD FOR USE AS BIOCONTROL AGENT

(75) Inventors: Mark Albert Vaeck, Elewijt; Wipa Chungjatupornchai, Gent, both of (BE); Lee McIntosh, East Lansing, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/837,625

(22) Filed: Feb. 18, 1992

Related U.S. Application Data

(63) Continuation of application No. 07/243,798, filed on Sep. 13, 1998, now abandoned, which is a continuation-in-part of application No. 07/021,405, filed on Mar. 4, 1987.

(51) Int. Cl.[7] .............................. A01N 63/00; C12N 1/21; C12N 15/32; C12N 15/74
(52) U.S. Cl. ................... 424/93.2; 435/69.1; 435/252.3; 435/320.1; 536/23.2; 536/23.71; 536/24.1
(58) Field of Search ................................ 424/93.2, 93.28; 435/69.1, 172.3, 252.3, 320.1, 822, 440, 468, 471, 91.1, 946; 536/23.1, 23.7, 23.71, 24.1

(56) References Cited

U.S. PATENT DOCUMENTS 4,778,759 A * 10/1988 Szalay et al. ................. 435/477
5,516,693 A * 5/1996 Vaeck et al. ............... 435/320.1

OTHER PUBLICATIONS

ATCC Catalog of Bacteria and Bacteriophages, 17th ed. (1989), pp. 248–249.*
Brock, T. D. Biology of Microorganisms. Prentice Hall, NJ (1979), pp. 627–629.*
Bold et al. Introduction to the Algae: Structure and Reproduction, Prentice Hall, NJ (1985), pp. 34–35, 38–39, and 47–51.*
Jannson et al. Plant Physiol. 85 (1987), 1021–1025.*
Sugita et al. Mol. Gen. Genet. 195 (1984), 308–313.*
Thomson et al. EMBO J. 6 (1986), 2519–2523.*
Ward et al. FEBS 175 (1984), 377–382.*
Wu et al. FEBS 190 (1985), 232–236.*

* cited by examiner

*Primary Examiner*—John L. LeGuyader
*Assistant Examiner*—Thomas G. Larson
(74) *Attorney, Agent, or Firm*—Ian C. McLeod

(57) ABSTRACT

Cyanobacteria incorporating a gene from Bacillus sp. encoding for insecticidal proteins (endotoxins) is described. The endotoxins are particularly effective against Diptera (mosquito) larvae. Recombinant vectors for transforming DNA fragments of the endotoxin gene or genes into the Cyanobacterium are described. The Cyanobacteria are easily grown in ponds or the like where the mosquitos or other insects breed. Additionally, these Cyanobacteria contain and express beside the endotoxin gene(s), a determined gene, the expression of which inhibits the herbicidal effects of glutamine synthetase inhibitors, enabling the Cyanobacteria to be selectively protected from competitive Cyanobacteria by treating them with the glutamine synthetase inhibitors

40 Claims, 24 Drawing Sheets

```
           10         20         30         40         50         60
GATAAGAATTGTTCATAGGAATCCGTATCAATTTTTTCAAGGAATATGTATTTGCACTTT 70         80         90        100        110        120
TGGTCTTTTTAAATCGTATGAATTCAAAATAGTTTATATCAATCTTTGTTACACCAGAAA 130        140        150        160        170        180
AAGATTGTATCCAATGTGAATATGGGAGGAATAAATATGAATTCAGGCTATCCGTTAGCG
                                       MetAsnSerGlyTyrProLeuAla
          190        200        210        220        230        240
AATGACTTACAAGGGTCAATGAAAAACACGAACTATAAAGATTGGCTAGCCATGTGTGAA
AsnAspLeuGlnGlySerMetLysAsnThrAsnTyrLysAspTrpLeuAlaMetCysGlu
          250        260        270        280        290        300
AATAACCAACAGTATGGCGTTAATCCAGCTGCGATTAATTCTTCTTCAGTTAGTACCGCT
AsnAsnGlnGlnTyrGlyValAsnProAlaAlaIleAsnSerSerSerValSerThrAla
          310        320        330        340        350        360
TTAAAAGTAGCTGGAGCTATCCTTAAATTTGTAAACCCACCTGCAGGTACTGTCTTAACC
LeuLysValAlaGlyAlaIleLeuLysPheValAsnProProAlaGlyThrValLeuThr
          370        380        390        400        410        420
GTACTTAGCGCGGTGCTTCCTATTCTTTGGCCGACTAATACTCCAACGCCTGAAAGAGTT
ValLeuSerAlaValLeuProIleLeuTrpProThrAsnThrProThrProGluArgVal
          430        440        450        460        470        480
TGGAATGATTTCATGACCAATACAGGGAATCTTATTGATCAAACTGTAACAGCTTATGTA
TrpAsnAspPheMetThrAsnThrGlyAsnLeuIleAspGlnThrValThrAlaTyrVal
          490        500        510        520        530        540
CGAACAGATGCAAATGCAAAAATGACGGTTGTGAAAGATTATTTAGATCAATATACAACT
ArgThrAspAlaAsnAlaLysMetThrValValLysAspTyrLeuAspGlnTyrThrThr
          550        560        570        580        590        600
AAATTTAACACTTGGAAAAGAGAGCCTAATAACCAGTCCTATAGAACAGCAGTAATAACT
LysPheAsnThrTrpLysArgGluProAsnAsnGlnSerTyrArgThrAlaValIleThr
          610        620        630        640        650        660
CAATTTAACTTAACCAGTGCCAAACTTCGAGAGACCGCAGTTTATTTTAGCAACTTAGTA
GlnPheAsnLeuThrSerAlaLysLeuArgGluThrAlaValTyrPheSerAsnLeuVal
          670        680        690        700        710        720
GGTTATGAATTATTGTTATTACCAATATACGCACAAGTAGCAAATTTCAATTTACTTTTA
GlyTyrGluLeuLeuLeuLeuProIleTyrAlaGlnValAlaAsnPheAsnLeuLeuLeu
          730        740        750        760        770        780
ATAAGAGATGGCCTCATAAATGCACAAGAATGGTCTTTAGCACGTAGTGCTGGTGACCAA
IleArgAspGlyLeuIleAsnAlaGlnGluTrpSerLeuAlaArgSerAlaGlyAspGln
          790        800        810        820        830        840
CTATATAACACTATGGTGCAGTACACTAAAGAATATATTGCACATAGCATTACATGGTAT
LeuTyrAsnThrMetValGlnTyrThrLysGluTyrIleAlaHisSerIleThrTrpTyr
          850        860        870        880        890        900
AATAAAGGTTTAGATGTACTTAGAAATAAATCTAATGGACAATGGATTACGTTTAATGAT
AsnLysGlyLeuAspValLeuArgAsnLysSerAsnGlyGlnTrpIleThrPheAsnAsp
                                                              ---
```

FIG. 2a-I

```
              910       920       930       940       950       960
     TATAAAAGAGAGATGACTATTCAAGTATTAGATATACTCGCTCTTTTTGCCAGTTATGAT
     TyrLysArgGluMetThrIleGlnValLeuAspIleLeuAlaLeuPheAlaSerTyrAsp
              970       980       990      1000      1010      1020
     CCACGTCGATACCCTGCGGACAAAATAGATAATACGAAACTATCAAAAACAGAATTTACA
     ProArgArgTyrProAlaAspLysIleAspAsnThrLysLeuSerLysThrGluPheThr
             1030      1040      1050      1060      1070      1080
     AGAGAGATTTATACAGCTTTAGTAGAATCTCCTTCTAGTAAATCTATAGCAGCACTGGAG
     ArgGluIleTyrThrAlaLeuValGluSerProSerSerLysSerIleAlaAlaLeuGlu
             1090      1100      1110      1120      1130      1140
     GCAGCACTTACACGAGATGTTCATTTATTCACTTGGCTAAAGAGAGTAGATTTCTGGACC
     AlaAlaLeuThrArgAspValHisLeuPheThrTrpLeuLysArgValAspPheTrpThr
             1150      1160      1170      1180      1190      1200
     AATACTATATATCAAGATTTAAGATTTTTATCTGCCAATAAAATTGGGTTTTCATATACA
     AsnThrIleTyrGlnAspLeuArgPheLeuSerAlaAsnLysIleGlyPheSerTyrThr
             1210      1220      1230      1240      1250      1260
     AATTCTTCTGCAATGCAAGAAAGTGGAATTTATGGAAGTTCTGGTTTTGGTTCAAATCTT
     AsnSerSerAlaMetGlnGluSerGlyIleTyrGlySerSerGlyPheGlySerAsnLeu
             1270      1280      1290      1300      1310      1320
     ACTCATCAAATTCAACTTAATTCTAATGTTTATAAAACTTCTATCACAGATACTAGCTCC
     ThrHisGlnIleGlnLeuAsnSerAsnValTyrLysThrSerIleThrAspThrSerSer
             1330      1340      1350      1360      1370      1380
     CCCTCTAATCGAGTTACAAAAATGGATTTCTACAAAATTGATGGTACTCTTGCCTCTTAT
     ProSerAsnArgValThrLysMetAspPheTyrLysIleAspGlyThrLeuAlaSerTyr
             1390      1400      1410      1420      1430      1440
     AATTCAAATATAACACCAACTCCTGAAGGTTTAAGGACCACATTTTTTGGATTTTCAACA
     AsnSerAsnIleThrProThrProGluGlyLeuArgThrThrPhePheGlyPheSerThr
             1450      1460      1470      1480      1490      1500
     AATGAGAACACACCTAATCAACCAACTGTAAATGATTATACGCATATTTTAAGCTATATA
     AsnGluAsnThrProAsnGlnProThrValAsnAspTyrThrHisIleLeuSerTyrIle
             1510      1520      1530      1540      1550      1560
     AAAACTGATGTTATAGATTATAACAGTAACAGGGTTTCATTTGCTTGGACACATAAGATT
     LysThrAspValIleAspTyrAsnSerAsnArgValSerPheAlaTrpThrHisLysIle
             1570      1580      1590      1600      1610      1620
     GTTGACCCTAATAATCAAATATACACAGATGCTATCACACAAGTTCCGGCCGTAAAATCT
     ValAspProAsnAsnGlnIleTyrThrAspAlaIleThrGlnValProAlaValLysSer
             1630      1640      1650      1660      1670      1680
     AACTTCTTGAATGCAACAGCTAAAGTAATCAAGGGACCTGGTCATACAGGGGGGGATCTA
     AsnPheLeuAsnAlaThrAlaLysValIleLysGlyProGlyHisThrGlyGlyAspLeu
             1690      1700      1710      1720      1730      1740
     GTTGCTCTTACAAGCAATGGTACTCTAGCAGGCAGAATGGAGATTCAATGTAAAACAAGT
     ValAlaLeuThrSerAsnGlyThrLeuSerGlyArgMetGluIleGlnCysLysThrSer
             1750      1760      1770      1780      1790      1800
     ATTTTTAATGATCCTACAAGAAGTTACGGATTACGCATACGTTATGCTGCAAATAGTCCA
     IlePheAsnAspProThrArgSerTyrGlyLeuArgIleArgTyrAlaAlaAsnSerPro
```

FIG. 2a-2

```
       1810      1820      1830      1840      1850      1860
ATTGTATTGAATGTATCATATGTATTACAAGGAGTTTCTAGAGGAACAACGATTAGTACA
IleValLeuAsnValSerTyrValLeuGlnGlyValSerArgGlyThrThrIleSerThr
       1870      1880      1890      1900      1910      1920
GAATCTACGTTTTCAAGACCTAATAATATAATACCTACAGATTTAAAATATGAAGAGTTT
GluSerThrPheSerArgProAsnAsnIleIleProThrAspLeuLysTyrGluGluPhe
       1930      1940      1950      1960      1970      1980
AGATACAAAGATCCTTTTGATGCAATTGTACCGATGAGATTATCTTCTAATCAACTGATA
ArgTyrLysAspProPheAspAlaIleValProMetArgLeuSerSerAsnGlnLeuIle
       1990      2000      2010      2020      2030      2040
ACTATAGCTATTCAACCATTAAACATGACTTCAAATAATCAAGTGATTATTGACAGAATC
ThrIleAlaIleGlnProLeuAsnMetThrSerAsnAsnGlnValIleIleAspArgIle
       2050      2060      2070      2080      2090      2100
GAAATTATTCCAATCACTCAATCTGTATTAGATGAGACAGAGAACCAAAATTTAGAATCA
GluIleIleProIleThrGlnSerValLeuAspGluThrGluAsnGlnAsnLeuGluSer
       2110      2120      2130      2140      2150      2160
GAACGAGAAGTTGTGAATGCACTGTTTACAAATGACGCGAAAGATGCATTAAACATTGGA
GluArgGluValValAsnAlaLeuPheThrAsnAspAlaLysAspAlaLeuAsnIleGly
       2170      2180      2190      2200      2210      2220
ACGACAGATTATGACATAGATCAAGCCGCAAATCTTGTGGAATGTATTTCTGAAGAATTA
ThrThrAspTyrAspIleAspGlnAlaAlaAsnLeuValGluCysIleSerGluGluLeu
       2230      2240      2250      2260      2270      2280
TATCCAAAAGAAAAAATGCTGTTATTAGATGAAGTTAAAAATGCGAAACAACTTAGTCAA
TyrProLysGluLysMetLeuLeuLeuAspGluValLysAsnAlaLysGlnLeuSerGln
       2290      2300      2310      2320      2330      2340
TCTCGAAATGTACTTCAAAACGGGGATTTTGAATCGGCTACGCTTGGTTGGACAACAAGT
SerArgAsnValLeuGlnAsnGlyAspPheGluSerAlaThrLeuGlyTrpThrThrSer
       2350      2360      2370      2380      2390      2400
GATAATATCACAATTGAAGAAGATGATCCTATTTTTAAAGGGCATTACCTTCATATGTCT
AspAsnIleThrIleGlnGluAspAspProIlePheLysGlyHisTyrLeuHisMetSer
       2410      2420      2430      2440      2450      2460
GGGGCGAGAGACATTGATGGTACGATATTTCCGACCTATATATTCCAAAAAATTGATGAA
GlyAlaArgAspIleAspGlyThrIlePheProThrTyrIlePheGlnLysIleAspGlu
       2470      2480      2490      2500      2510      2520
TCAAAATTAAAACCGTATACACGTTACCTAGTAAGGGGATTTGTAGGAAGTAGTAAAGAT
SerLysLeuLysProTyrThrArgTyrLeuValArgGlyPheValGlySerSerLysAsp
       2530      2540      2550      2560      2570      2580
GTAGAACTAGTGGTTTCACGCTATGGGGAAGAAATTGATGCCATCATGAATGTTCCAGCT
ValGluLeuValValSerArgTyrGlyGluGluIleAspAlaIleMetAsnValProAla
       2590      2600      2610      2620      2630      2640
GATTTAAACTATCTGTATCCTTCTACCTTTGATTGTGAAGGGTCTAATCGTTGTGAGACG
AspLeuAsnTyrLeuTyrProSerThrPheAspCysGluGlySerAsnArgCysGluThr
       2650      2660      2670      2680      2690      2700
TCCGCTGTGCCGGCTAACATTGGGAACACTTCTGATATGTTGTATTCATGCCAATATGAT
SerAlaValProAlaAsnIleGlyAsnThrSerAspMetLeuTyrSerCysGlnTyrAsp
       2710      2720      2730      2740      2750      2760
ACAGGGAAAAAGCATGTCGTATGTCAGGATTCCCATCAATTTAGTTTCACTATTGATACA
ThrGlyLysLysHisValValCysGlnAspSerHisGlnPheSerPheThrIleAspThr
```

FIG. 2a-3

```
      2770      2780      2790      2800      2810      2820
GGGGCATTAGATACAAATGAAAATATAGGGGTTTGGGTCATGTTTAAAATATCTTCTCCA
GlyAlaLeuAspThrAsnGluAsnIleGlyValTrpValMetPheLysIleSerSerPro
      2830      2840      2850      2860      2870      2880
GATGGATACGCATCATTAGATAATTTAGAAGTAATTGAAGAAGGGCCAATAGATGGGGAA
AspGlyTyrAlaSerLeuAspAsnLeuGluValIleGluGluGlyProIleAspGlyGlu
      2890      2900      2910      2920      2930      2940
GCACTGTCACGCGTGAAACACATGGAGAAGAAATGGAACGATCAAATGGAAGCAAAACGT
AlaLeuSerArgValLysHisMetGluLysLysTrpAsnAspGlnMetGluAlaLysArg
      2950      2960      2970      2980      2990      3000
TCGGAAACACAACAAGCATATGATGTAGCGAAACAAGCCATTGATGCTTTATTCACAAAT
SerGluThrGlnGlnAlaTyrAspValAlaLysGlnAlaIleAspAlaLeuPheThrAsn
      3010      3020      3030      3040      3050      3060
GTACAAGATGAGGCTTTACAGTTTGATACGACACTCGCTCAAATTCAGTACGCTGAGTAT
ValGlnAspGluAlaLeuGlnPheAspThrThrLeuAlaGlnIleGlnTyrAlaGluTyr
      3070      3080      3090      3100      3110      3120
TTGGTACCATCGATTCCATATGTGTACAATGATTGGTTGTCAGATGTTCCAGGTATGAAT
LeuValGlnSerIleProTyrValTyrAsnAspTrpLeuSerAspValProGlyMetAsn
      3130      3140      3150      3160      3170      3180
TATGATATCTATGTAGAGTTGGATGCACGAGTGGCACAAGCGCGTTATTTGTATGATACA
TyrAspIleTyrValGluLeuAspAlaArgValAlaGlnAlaArgTyrLeuTyrAspThr
      3190      3200      3210      3220      3230      3240
AGAAATATTATTAAAAATGGTGATTTTACACAAGGGGTAATGGGGTGGCATGTAACTGGA
ArgAsnIleIleLysAsnGlyAspPheThrGlnGlyValMetGlyTrpHisValThrGly
      3250      3260      3270      3280      3290      3300
AATGCAGACGTACAACAAATAGATGGTGTTTCTGTATTGGTTCTATCTAATTGGAGTGCT
AsnAlaAspValGlnGlnIleAspGlyValSerValLeuValLeuSerAsnTrpSerAla
      3310      3320      3330      3340      3350      3360
GGCGTATCTCAAAATGTCCATCTCCAACATAATCATGGGTATGTCTTACGTGTTATTGCC
GlyValSerGlnAsnValHisLeuGlnHisAsnHisGlyTyrValLeuArgValIleAla
      3370      3380      3390      3400      3410      3420
AAAAAAGAAGGACCTGGAAATGGGTATGTCACGCTTATGGATTGTGAGGAGAATCAAGAA
LysLysGluGlyProGlyAsnGlyTyrValThrLeuMetAspCysGluGluAsnGlnGlu
      3430      3440      3450      3460      3470      3480
AAATTGACGTTTACGTCTTGTGAAGAAGGATATATTACGAAGACAGTAGATGTATTCCCA
LysLeuThrPheThrSerCysGluGluGlyTyrIleThrLysThrValAspValPhePro
      3490      3500      3510      3520      3530      3540
GATACAGATCGTGTACGAATTGAGATAGGCGAAACCGAAGGTTCGTTTTATATCGAAAGC
AspThrAspArgValArgIleGluIleGlyGluThrGluGlySerPheTyrIleGluSer
      3550      3560      3570      3580      3590      3600
ATTGAATTAATTTGCATGAACGAGTGATTAATAAAAAATAACTAAAGCTTTAAAAACCAT
IleGluLeuIleCysMetAsnGlu***
      3610      3620      3630      3640      3650      3660
GGAGAAAGTTTTCTCCATGGTTTTAATTTCTGCATTTATTAATTCTGGTACAAAAAATA
      3670      3680         0         0         0         0
TATAGAAAACATAAAAAATAGATA
```

FIG. 2a-4

```
         10         20         30         40         50         60
MNSGYPLAND LQGSMKNTNY KDWLAMCENN QQYGVNPAAI NSSSVSTALK VAGAILKFVN 70         80         90        100        110        120
PPAGTVLTVL SAVLPILWPT NTPTPERVWN DFMTNTGNLI DQTVTAYVRT DANAKMTVVK 130        140        150        160        170        180
DYLDQYTTKF NTWKREPNNQ SYRTAVITQF NLTSAKLRET AVYFSNLVGY ELLLLPIYAQ 190        200        210        220        230        240
VANFNLLLIR DGLINAQEWS LARSAGDQLY NTMVQYTKEY IAHSITWYNK GLDVLRNKSN 250        260        270        280        290        300
GQWITFNDYK REMTIQVLDI LALFASYDPR RYPADKIDNT KLSKTEFTRE IYTALVESPS 310        320        330        340        350        360
SKSIAALEAA LTRDVHLFTW LKRVDFWTNT IYQDLRFLSA NKIGFSYTNS SAMQESGIYG 370        380        390        400        410        420
SSGFGSNLTH QIQLNSNVYK TSITDTSSPS NRVTKMDFYK IDGTLASYNS NITPTPEGLR 430        440        450        460        470        480
TTFFGFSTNE NTPNQPTVND YTHILSYIKT DVIDYNSNRV SFAWTHKIVD PNNQIYTDAI 490        500        510        520        530        540
TQVPAVKSNF LNATAKVIKG PGHTGGDLVA LTSNGTLSGR MEIQCKTSIF NDPTRSYGLR 550        560        570        580        590        600
IRYAANSPIV LNVSYVLQGV SRGTTISTES TFSRPNNIIP TDLKYEEFRY KDPFDAIVPM 610        620        630        640        650        660
RLSSNQLITI AIQPLNMTSN NQVIIDRIEI IPITQSVLDE TENQNLESER EVVNALFTND 670        680        690        700        710        720
AKDALNIGTT DYDIDQAANL VECISEELYP KEKMLLLDEV KNAKQLSQSR NVLQNGDFES 730        740        750        760        770        780
ATLGWTTSDN ITIQEDDPIF KGHYLHMSGA RDIDGTIFPT YIFQKIDESK LKPYTRYLVR 790        800        810        820        830        840
GFVGSSKDVE LVVSRYGEEI DAIMNVPADL NYLYPSTFDC EGSNRCETSA VPANIGNTSD 850        860        870        880        890        900
MLYSCQYDTG KKHVVCQDSH QFSFTIDTGA LDTNENIGVW VMFKISSPDG YASLDNLEVI 910        920        930        940        950        960
EEGPIDGEAL SRVKHMEKKW NDQMEAKRSE TQQAYDVAKQ AIDALFTNVQ DEALQFDTTL 970        980        990       1000       1010       1020
AQIQYAEYLV QSIPYVYNDW LSDVPGMNYD IYVELDARVA QARYLYDTRN IIKNGDFTQG 1030       1040       1050       1060       1070       1080
VMGWHVTGNA DVQQIDGVSV LVLSNWSAGV SQNVHLQHNH GYVLRVIAKK EGPGNGYVTL 1090       1100       1110       1120       1130          0
MDCEENQEKL TFTSCEEGYI TKTVDVFPDT DRVRIEIGET EGSFYIESIE LICMNE
```

FIG. 2b

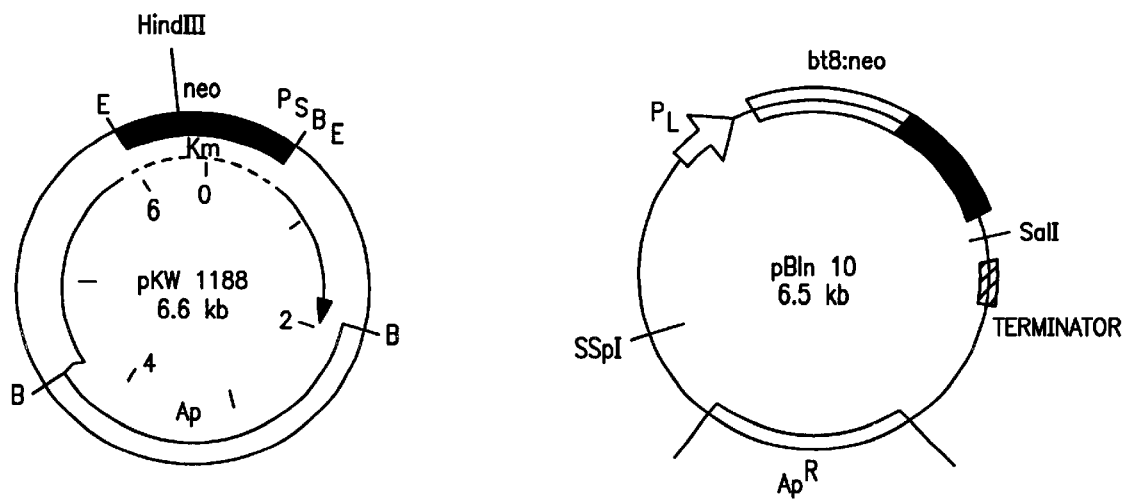
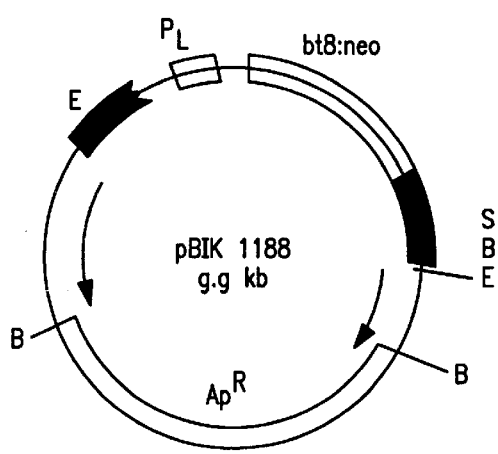
FIG. 6

B.t. israelensis 27 kDa toxin gene

HaeIII — 880 bp — TaqI

StuI (1520) — PpsbA-2 → TaqI (2029)

HincII (1053) — terminator — StuI (1350)

FIG. 16

HYBRID GENES INCORPORATING A DNA FRAGMENT CONTAINING AT LEAST ONE GENE ENCODING AN INSECTICIDAL PROTEIN AND A GENE ENCODING A GLUTAMINE SYNTHASE INHIBITOR, PLASMIDS, TRANSFORMED CYANOBACTERIA EXPRESSING SUCH PROTEINS AND METHOD FOR USE AS BIOCONTROL AGENT

CROSS-REFERENCE TO RELATED APPLICATION

This is a continuation of application(s) Ser. No. 07/243,798 filed on Sep. 13, 1988, abandoned, which is a continuation-in-part of U.S. application Ser. No. 07/021,405, filed Mar. 4, 1987.

BACKGROUND OF THE INVENTION

(1) Field of the Invention

The present invention relates to a hybrid gene incorporating a DNA fragment containing a gene coding for an insecticidal protein, more specifically a gene coding for an endotoxin active against Diptera. It also relates more particularly to recombinant vectors containing such gene or DNA fragment. It also relates to pro- and eukaryotic cells modified by these recombinant DNA vectors.

(2) Prior Art

The usefulness of *Bacillus thuringienses* endotoxins to control insect pests has been demonstrated over a wide range of crop and environmental pests.

*Bacillus thuringienses* var. *israelensis* has been used as a biological insecticide to combat mosquito and black fly larvae in swamps, which are a real problem for human health, especially in tropical areas, and cause malaria and other diseases.

Commercial formulations consist of a culture of *Bacillus thuringiensis* var. *israelensis* bacterium in the sporulated stage consisting of spores and crystals. These crystals consist of proteins which have insect toxicity. These proteins act on the insect midguts when ingested by the larvae.

The main drawback of this approach is the fact that *Bacillus thuringiensis* bacterium is unstable in the environment (susceptible to U.V., washed away by intensive rains, etc.). Therefore one has to spray regularly which makes this method very expensive.

Strains of the Gram-positive bacterium *Bacillus thuringiensis* (B.t.) produce intracellular protein crystals during the process of sporulation (Bulla et al. J. Bacteriol. 130, 375–383 (1977)). These crystal proteins, termed δ-endotoxins, are toxic to a wide variety of Lepidoptera insects (Dulmage, et al., in Genetics and Relation to Insect Management (Hoy and Mekelvey, Jr. eds.), Rockefeller Foundation, New York, pp. 116–127 (1979)), some Diptera and Coleoptera. The endotoxins produced by different strains of B.t. may differ in their molecular structure and in their insect host range. In addition, one B.t. isolate may produce distinct types of crystal proteins.

*Bacillus thuringiensis* var. *israelensis* (Goldberg-Margalit, Mosquito News 37, 353–358 (1977)), produces crystals that are highly toxic to larvae of mosquitos and black flies. In addition, the solubilized crystal proteins exhibit hemolytic activity and cytotoxicity towards mammalian cells (Thomas and Ellar, J. Cell Sci., 60, 181–197 (1983)).

B.t. *israelensis* crystals contain three main polypeptides of 130, 65 and 28 kDa with distinct antigenic properties. Controversy still exists on which component is responsible for the potent mosquitocidal activity in B.t. *israelensis* crystals. Originally, both insect toxicity and homolytic activity were attributed to the 28 kDa protein (Yamamoto, et al, Curr. Microbiol. 9, 279–284 (1983); Armstrong, et al, J. Bacteriol. 161, 39–46 (1985)). This was confirmed recently by molecular cloning and characterization of the B.t. *israelensis* gene encoding the 28 kDa crystal protein (Ward et al., FEBS, 175, 377–382 (1984); Ward and Ellar, J. Mol. Biol. 191: 1–11, 1986)). On the other hand, using purified crystal protein fractions, Visser et al. (Visser et al., FEMS Microbiol. Lett., 30, 211–214 (1986)) showed that, while the 28 kDa protein is hemolytic, the specific mosquitocidal activity resides entirely in the protein of 130 kDa.

A method has been described (McIntosh et al., in Molecular Form and Function of the Plant Genome; Plenum Press, New York, pp. 335–346 (1985)) for targeting insertions of foreign DNA into the chromosome of the Cyanobacterium Synechocystis 6803. This organism has a transformation system that enables it to take up exogenous DNA spontaneously. Donor DNA molecules were constructed by inserting a bacterial gene for kanamycin resistance into fragments of chromosomal DNA from the Cyanobacterium. Recipient cells were transformed to kanamycin-resistance with a frequency as high as four transformants per thousand cells. Analysis of DNA from transformants by transfer hybridization showed that the kanamycin-resistance gene was inserted in the cyanobacterial chromosome. Integration occurred by replacement of chromosomal DNA with homologous DNA that contained the foreign insert.

The ability of some Cyanobacterial species to take up exogenous DNA is central to the genetic modification. In many Cyanobacteria, DNA added to the growth medium enters cells by a naturally-occurring mechanism, as shown by using DNA isolated from spontaneous antibiotic-resistant mutants to transfer the resistant phenotype to sensitive cells (Shestakov and Khyen, Mol. Gen. Genet., 107, 372–375 (1970); Astier and Espardellier, C. R. Acad. Sci. Paris, 282, 795–797 (1976); Stevens and Porter, PNAS, USA, 77, 6052–6056 (1980); Griogoreiva and Shestakov, FEMS Microbiol. Lett. 13, 367–370 (1982)). This indicates that mutations in native Cyanobacterial genes can be introduced into wild-type cells. Cyanobacteria can also take up foreign DNA, as demonstrated by transformation with recombinant plasmids consisting of bacterial antibiotic-resistance genes linked to native Cyanobacterial plasmids (Buzby et al., J. Bacteriol. 154, 1446–1450 (1983); Van de Hondel et al., PNAS, USA, 77, 1570–1574 (1980)). In the cases, transformants were easily recovered on medium containing the appropriate antibiotics and were shown to harbor the recombinant plasmids. Another mechanism for DNA uptake, by conjugal transfer from *E. coli* cells, has been demonstrated recently with recombinant plasmids in a number of Cyanobacterial species (Wolk et al., PNAS, USA, 81, 1561–1565 (1984)). Whereas Cyanobacterial plasmids could be useful for complementation studies, they are less valuable for modifying genes resident on the chromosome.

In bacteria, plasmids have been used to construct insertion mutations in chromosomal genes (Ruvkun and Ausubel, Nature 289, 85–88 (1981)). This is accomplished by inserting an antibiotic resistance gene into a chromosomal gene that has been cloned in the plasmid, then the plasmid is introduced into wild-type cells to allow the antibiotic resistance gene to move from plasmid to chromosome by homologous recombination, finally recombinants are selected by curing cells of the plasmid while continuing to select for antibiotic resistance. This procedure has not been used in Cyanobacteria, in part because there is no efficient way to cure Cyanobacteria of autonomously replicating plasmids (Tandenau de Marsac et al., Gene, 20, 111–119 (1982)).

In an effort to develop a procedure for altering chromosomal genes in Cyanobacteria, Williams and Szalay (Williams and Szalay, Gene, 24, 37–51 (1983)) studied transformation in Synechococcus R2 using bacterial antibiotic resistance genes linked to fragments of Synechococcus R2 chromosomal DNA. It was found that the foreign DNA integrated efficiently into the Synechococcus R2 chromosome by homologous recombination and that, depending on the position of the resistance gene within the Cyanobacterial DNA, mutant transformants could be constructed (Williams and Szalay, Gene, 24, 37–51 (1983); and unpublished results, JGKW). These characteristics of the Synechococcus R2 transformation system indicate that it should be possible to introduce modified genes into the chromosome of this organism.

Experiments reported by McIntosh (McIntosh, L. et al, The Molecular Form and Function of the Plant Genome, Plenum Press, N. Y. 335–346 (1985)) show the Synchocystis 6803 is able to assimilate insertions of foreign DNA into its chromosome by homologous recombination, much as described in Synechococcus R2.

OBJECTS

It is one object of the invention to provide novel chimeric genes coding for a mosquitocidal protein, preferentially protein of *Bacillus thuringiensis*.

Another object of the present invention is to provide novel hybrid plasmid vectors containing said chimeric genes, said vectors allowing the integration of said chimeric genes in the genome or remaining extrachromosomic.

A further object of the present invention is to provide Cyanobacteria transformed with said plasmids or said chimeric genes and a process for controlling mosquitos which comprises the use of said transformed Cyanobacteria.

Other objectives, features and advantages of the present invention will become apparent to those skilled in the art from the following description taken in conjunction with the accompanying drawings.

BRIEF DESCRIPTION OF THE DRAWINGS

FIG. 2*a* shows a DNA sequence and deduced amino acid sequence of the 130 kd B.t. *israelensis* toxin gene (Bt8). The putative ribosome binding site is underlined (position 145–149).

FIG. 2*b* shows the amino-acid sequence of Bt8.

FIG. 6 shows the construction of pBlK 1188.

FIG. 16 shows cloning of the 27 kDa toxin gene into the pUC19 vector containing the psbA-2 promoter sequences, as shown in FIG. 10.

SUMMARY OF THE INVENTION

Figure 1:
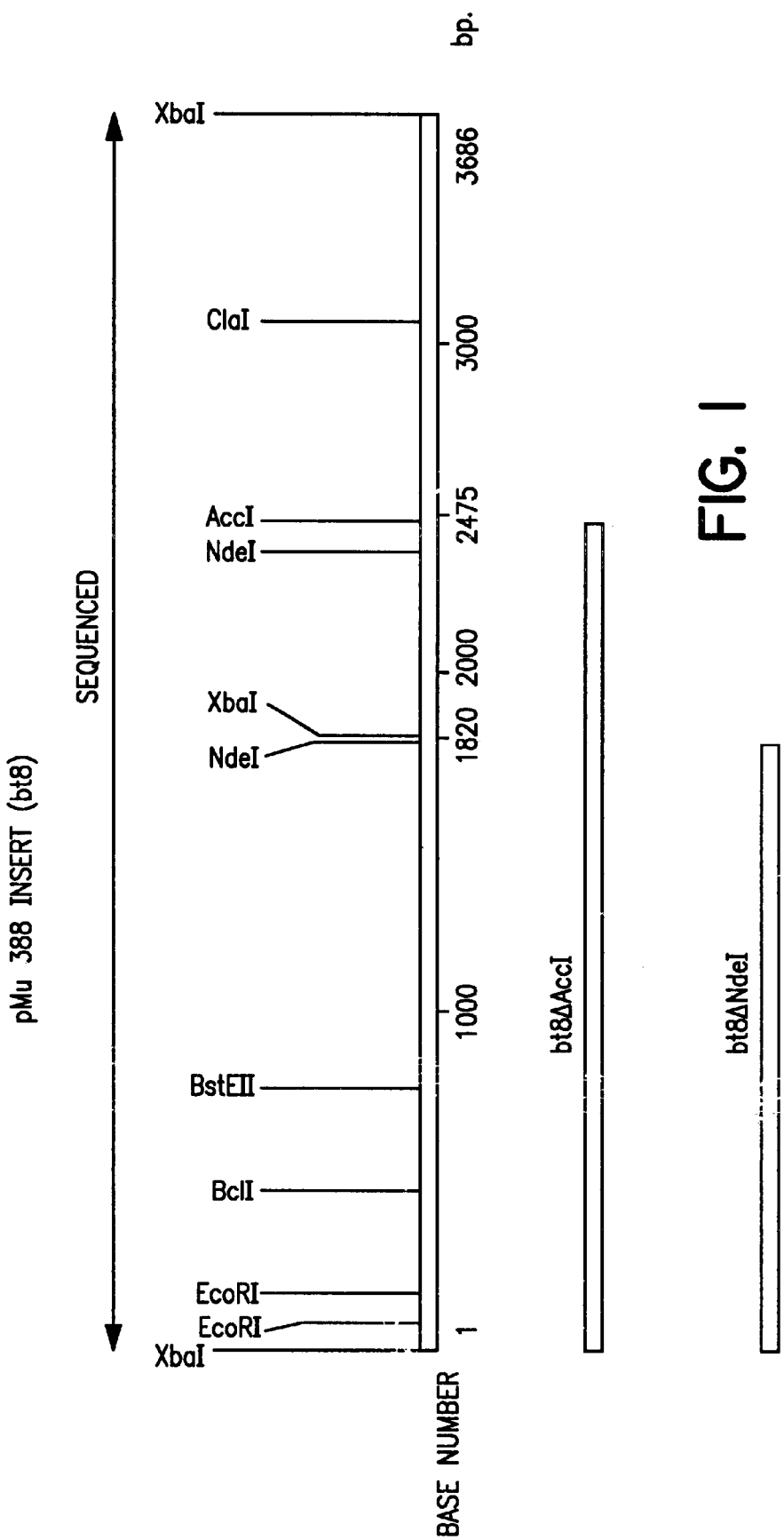
FIG. 1 shows a restriction enzyme map of the XbaI insert in clone pMU388. Gene fragments contained in 2 deletion clones (Bt8 AccI and Bt8 NdeI) are also represented. Toxicity to mosquito larvae of *E. coli* cells containing the pUC12 with the different inserts is also indicated.

The present invention provides a chimeric gene capable of being expressed in Cyanobacteria cells comprising:
  a) a DNA fragment comprising a promoter region which is effective for expression of a DNA fragment in a Cyanobacterium; and
  b) at least one DNA fragment coding for an insecticidally active protein produced by a Bacillus strain, or for an insecticidally active truncated form of the above protein or for an active protein having substantial sequence homology thereto.

The present invention provides better control of mosquitos by the use of transformed blue-green algae.

Blue-green algae or Cyanobacteria are photosynthetic prokaryotic organisms. They constitute an important food base for mosquito larvae. A gene coding for a Bt endotoxin, active against mosquito, inserted in the genome of these organisms, represents an efficient way to combat larvae of mosquito. Since a number of mosquito species are important vectors of major human and animal diseases, and are living in regions difficult to control on a continuous base, a method which ensures a long-term (destruction) of this pest is attractive.

Indeed, the advantages of the use of toxins produced in a naturally occurring organism are multiple compared to the use of endotoxins in any other formulation form (e.g. sprays). The presence of the toxin in the food of the target insects guarantees direct uptake by the said insects. Moreover, it assures a more stable availability of the toxin in the vicinity since it is self replicating and floating at or near the water surface.

So the present invention provides a chimeric gene capable of being expressed in Cyanobacteria cells comprising:
  a) a DNA fragment comprising a promoter region which is effective for expression of a DNA fragment in a Cyanobacterium; and
  b) at least one DNA fragment coding for an insecticidally active protein produced by a Bacillus strain, or for an insecticidally active truncated form of the protein or for an active protein having substantial sequence homology thereto. Especially interesting are the chimeric genes wherein said DNA fragment b) codes for a protein produced by a strain of Bacillus thuringiensis var. israelensis.

The present invention concerns preferentially the gene encoding the protein having mosquitocidal activity which is named B.t. 8 from Bacillus thuringiensis var. israelensis, encoding a 130 kDa crystal protein which structure is shown in FIG. 2, together with a truncated form of this protein. Expression of the above cited proteins in Cyanobacteria needs to have methods for transformation of such organism.

The chimeric genes include those where DNA fragment b) codes for a protein from Bacillus especially Bacillus thuringiensis or Bacillus sphaericus, preferentially having anti-Diptera activity and especially those where DNA fragment b) codes for the protein named Bt8 corresponding to the structure shows in FIG. 2 and its truncated form with insecticidal activity.

Said chimeric genes include also those wherein DNA fragment b) is fused to a DNA fragment c) coding for a protein especially an enzyme capable of being expressed and permitting identification or selection of Cyanobacterium expressing DNA fragment b), especially those genes wherein the selectable or scorable marker is the neo gene.

It is known that amino-terminal fusions at the kanamycin resistance gene (neo gene) can generate fusion proteins that still confer kanamycin resistance in bacteria (Reiss et al., EMBO J. 3, p. 3317, 1984). Since kanamycin resistance is a most suitable selection marker both in bacteria and in Cyanobacteria, such gene fusions have promising applications. Indeed when using such NPTII fusion proteins to transform Cyanobacteria, a selection for kanamycin resistance allows direct selection for expression of the fusion product. Therefore, toxin gene fusions with neo may be used to transform Cyanobacteria and select for transformants expressing high levels of toxin, by selection for kanamycin resistance. This selection procedure is particularly useful in a "shotgun" approach whereby the fusion gene is inserted randomly behind Cyanobacterium DNA sequences before transformation. This allows to directly select for those constructs comprising the fusion gene behind a strong promoter inducing high levels of the fusion protein in Cyanobacteria.

Said DNA fragment b) is under the control of a promoter functional in Cyanobacterium, it may be promoter region derived from the gene which is naturally expressed in said Cyanobacteria such as the promoter sequence directing expression of the rubisco operon or a promoter region of another Cyanobacterium or from a different organism such bacteria or phages, for example the lambdaPL promoter is functional in Synechocystis.

Said chimeric genes may be introduced in Cyanobacteria by different method as described above especially by transformation using hybrid plasmids harboring the above chimeric genes. Such plasmids may be used for integration of the chimeric gene within the genome of Cyanobacteria, especially by homologous recombination. For such recombination hybrid plasmids comprise at least a chromosomic fragment of DNA of Cyanobacteria and especially the chimeric gene is situated within the chromosomic fragment of DNA. Said plasmid, without chromosomic fragment of Cyanobacterium DNA, may be used also as extra-chromosomic plasmids, for example with an origin of replication function in the Cyanobacterium.

Further, in accordance with the present invention there are provided Cyanobacterium which include in their cell genome or harbor a plasmid expressing the chimeric genes as described above. Among the Cyanobacteria, the following are preferably used: Synechocystis, Anacystis. But other species may also be used depending for example on the biotype: Synechococcus, Agmenelum, Aphanocapsa, Gloecapsa, Nostoc, Anabaena or Ffremyllia. Still further in accordance with the present invention, there are provided Cyanobacteria which include in their genome and express beside the chimeric genes described above, an additional chimeric gene encoding for a protein which inactivate the herbicidal activity of phosphinotricine, rendering these Cyanobacteria resistant to the herbicide Bialaphos.

Still further in accordance with the present invention, there are provided insecticidal compositions and methods using the transformed Cyanobacteria and their progeny. Said transformed Cyanobacteria may be used as viable inoculum to settle the regions, especially the swamps and all stagnant waters which promote the growth of mosquito larvae.

Said Cyanobacteria may also be used directly for the preparation of an insecticidal formulation in any type of composition.

EXAMPLE 1

Figure 5:
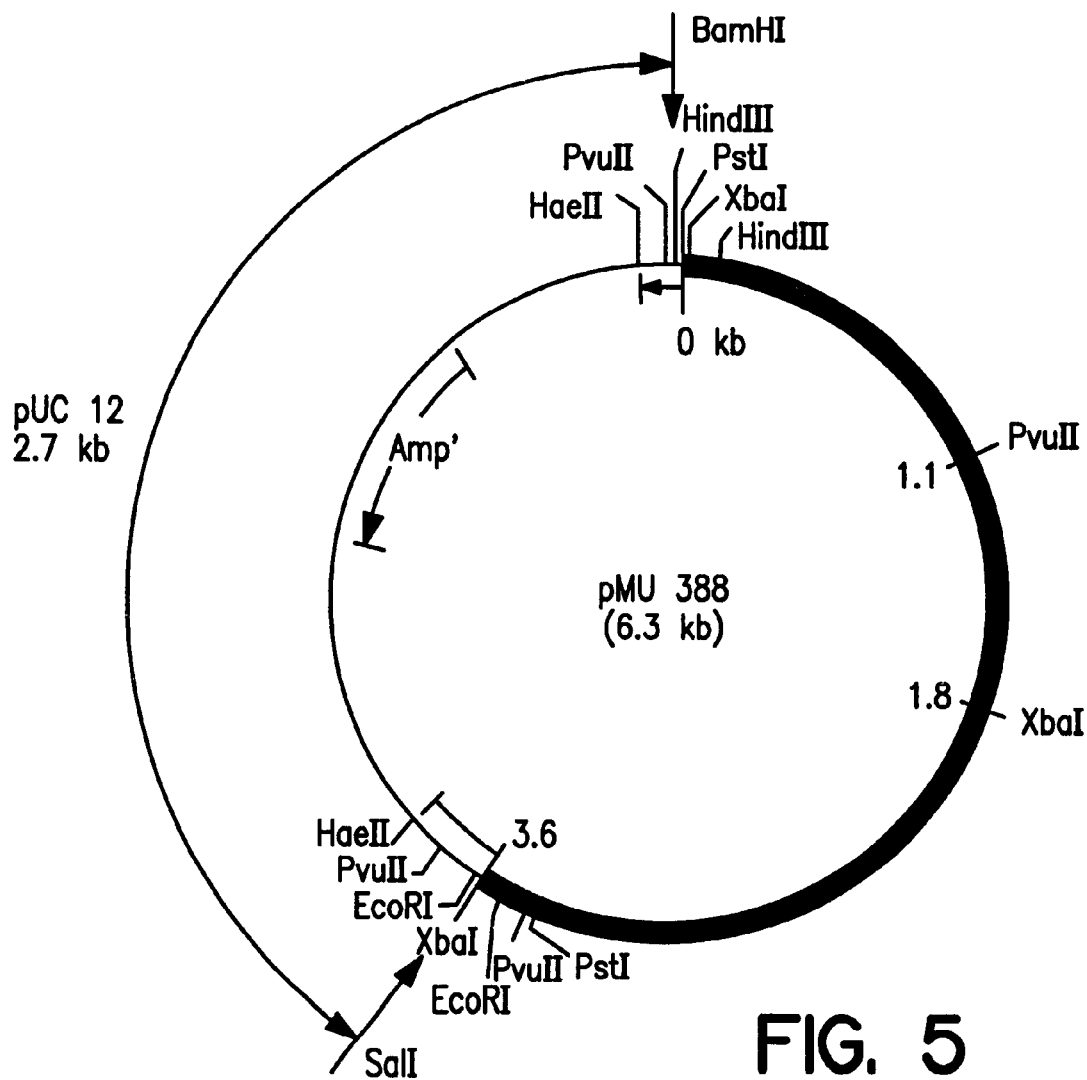
FIG. 5 shows the structure of pMU388 and pKW1188 synechocystis expression vector.

Expression in E. coli of a Bt.i 130 kDa Crystal Protein, Exhibiting Strong Mosquitocidal Activity From the Department of Biochemistry of the Faculty of Sciences of the Mahidol University of Bangkok, which is under the direction of Prof. Sakol Panyim, an E. coli clone K 514 containing plasmid pMU 388 was provided. This pMU 388 clone contains the pUC 12 which is ligated to a 110 Kb (±75 MDa) plasmid obtained from Bt. israelensis 4Q272 (obtained from the Bacillus Genetic Stock Center, Columbia, Ohio) (FIG. 5). Description of the construction of the clone is published in Angsuthanasombat et al., (1987), Mol. Gen. Genet. 208, 384–389.

The E. coli clone K 514 containing pMU 388 is highly toxic to larvae of Aedes aegyptil, (Table 1) and Anopheles, which presumes its harboring of the gene encoding the mosquitocidal crystal protein of Bt.i., inserted at the Xba site of pUC12. The restriction enzyme map of this Xba fragment is shown in FIG. 1. E. coli clone K514 (pMU388) is highly toxic to larvae of Aedes aegypti (Table 1), and therefore presumably harbors the gene for the mosquitocidal crystal protein of Bt.i. The pMU388 plasmid contains the pUC12 with an Xba insert of ±3.6 kb. The restriction enzyme map of this Xba fragment is shown in FIG. 1.

Analysis of total cell extract of E. coli K514 (pMU388) in SDS-polyacrylamide gel (SDS-PAGE), reveals an intense protein band of ±130 kDa, the same apparent molecular weight as one of the major crystal proteins of B.t.i. This protein is not present in a control E. coli K514, containing the pUC12 vector without insert.

This ±130 kDa protein, termed Bt8, represents between 5 and 10% of the total protein content of the E. coli cells. It is present in the bacterial cells as a precipitate and, after lysis of the cells, can be selectively solubilized using a buffer with alkaline pH (9–10) containing a reducing reagent (DTT, ME).

The same conditions also allow efficient solubilization of original B.t.i-crystals. The solubilized, semi-purified Bt8 protein, has been used for toxicity assays on A. aegypti larvae.

The LC50 value for solubilized Bt8 protein was 100 ng/ml significantly higher than for native B.t.i crystals. However, for solubilized B.t.i. crystals a much higher L.C.50 was also recorded (50 ng/ml see Table 2). Since mosquito larvae are filter feeders this can be explained by less efficient absorption of soluble protein as compared to particles. Indeed toxicity of Bt8 protein could be enhanced by precipitating with citric acid (5 ng/ml) and insolubilized Bt8 present in E. coli had an L.C.50 to the 5 ng/ml comparable of native Bti crystals (Table 2).

Purified Bt8 protein solubilized in alkaline buffer was assayed for toxicity on insect cell lines in vitro. While the 27 kDa toxin from Bti has been shown to cause complete lysis of Aedes albopictus cells at 50 ug/ml, Bt8 had no visible cytopathic effect even at 50 ug/ml. Therefore the Bt8 protein is clearly distinct from the 27 kDa Bti crystal protein in at least some of its functional properties.

Structural relationship between the cloned Bt8 polypeptide and the 130 kDa protein present in Bti crystals, was confirmed by immunological data. In Western blotting the Bt8 protein reacts strongly with a rabbit antiserum raised against crystal proteins of B.t.i. strain 4Q2–72. In addition a rabbit antiserum raised against the purified Bt8 protein also reacts strongly with the 130 kDa protein of Bti crystals. Therefore we have cloned and expressed in E. coli a Bti gene encoding a protein with functional and structural properties analogous to those of a major B.t.i crystal protein.

EXAMPLE 2

Nucleotide Sequence of the Toxin Gene

The complete 3.6 kb insert of clone pMU388 was sequenced.

The sequence (FIG. 2a-1) reveals a single large open reading frame. Four clustered potential ATG start points for translation, which could give rise to a ±130 kDa polypeptide, were identified at bp positions 142, 157, 199 and 232 (FIG. 2a-1). The ATG codon at position 157 was preceded by the consensus ribosome binding site GGAGG (bp 145–149). The reading frame starting at the ATG at bp position 157 and ending with a TGA stop codon at position 3565 encodes a protein of 1136 amino acids, with a predicted molecular mass of 127000 Da, which agrees well with the estimated mass of Bt8 determined in SDS-PAGE. Bt8 protein produced by E. coli K514 (pMU388) was purified and an N-terminal amino acid sequence was determined by gas-phase sequencing (J. Biol. Chem., 256: 7990–7997, 1987). The obtained sequence Met-Asn-Xaa-Gly-Tyr-Pro-Leu-Ala-Asn-Asp-Leu was identical to the one deduced from the DNA sequence starting at ATG position 157 (FIG. 2a) (Xaa indicates a residue which could not be unambiguously identified). The Bt8 gene is shown in FIG. 2b.

EXAMPLE 3

Identification of the Toxin Fragment Essential for Mosquitocidal Activity

The 130 kDa Lepodopteran specific B.t. endotoxins are protoxins, which after degradation by larval gut proteases yield smaller toxic polypeptides. We therefore investigated whether the 130 kDa mosquito specific Bt8 toxin would also generate smaller toxin fragments after protease treatment. Purified Bt8 protein was treated with either trypsin, chymotrypsin or with an extract containing proteolytic enzymes of A. aegypti larvae. After 1 h digestion at 37° C. the 130 kDa protein was completely degraded towards smaller polypeptide fragments. SDS-PAGE analysis revealed major protein bands of 48, 75 and 78 kDa for trypsin, 65 and 68 kDa for chymotrypsin and 45 and 72 kDa for mosquito gut proteases. When tested in insect assays all these digested samples showed toxicity levels on mosquito larvae, comparable to intact 130 kDA Bt8 protein. A similar level of toxicity (LC50 value of 1 ug/ml) was also achieved by a 80 kDa fragment, a spontaneous degradation product from Bt8, generated after prolonged storage of this protein at 4° C. (probably by E. coli proteases in the Bt8 sample).

Figure 3:
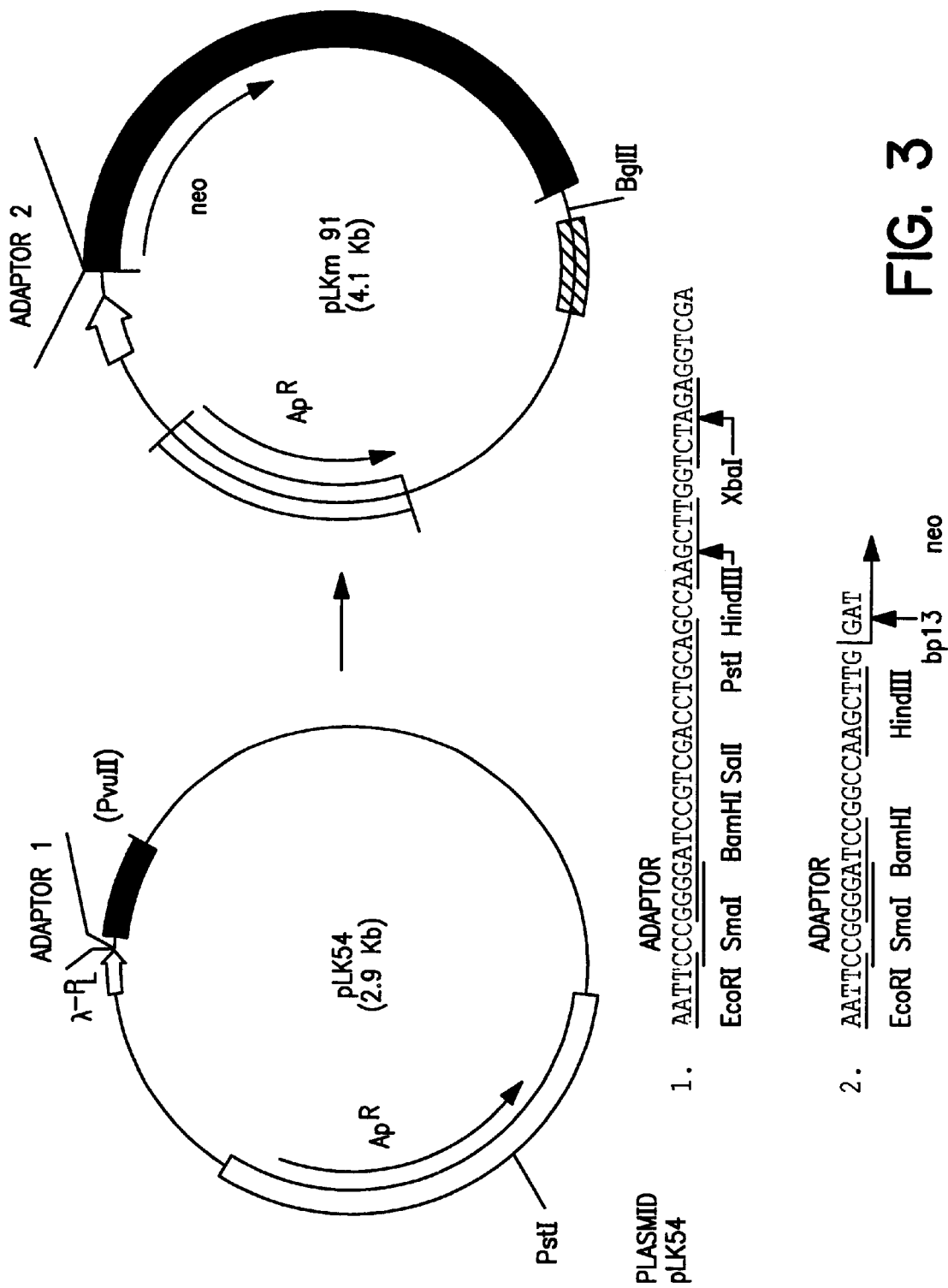
FIG. 3 shows the strategy used for the positioning of the toxin gene behind the lambdaPL promoter in pLKm91.
Figure 4:
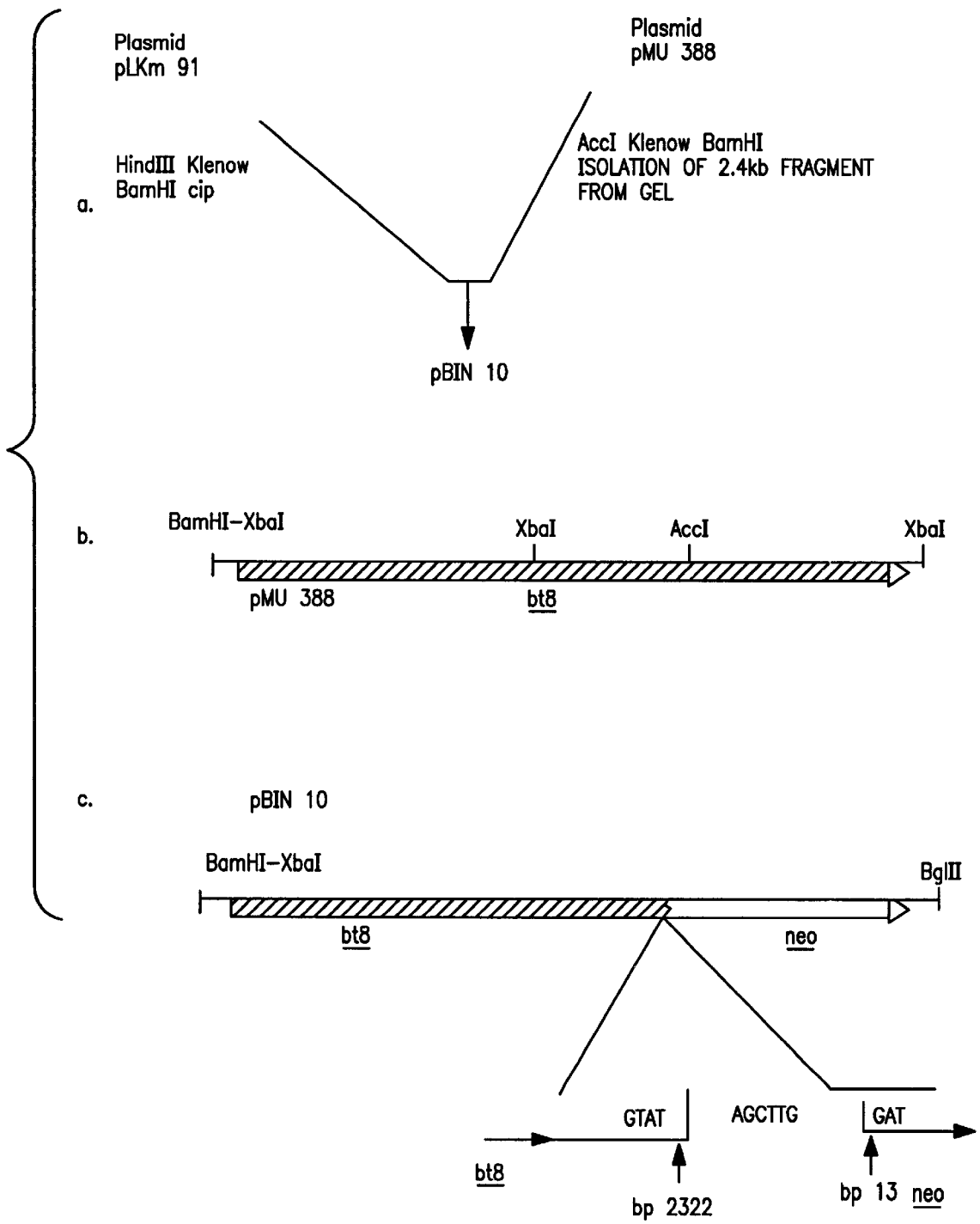
FIG. 4 shows the construction of Bt8: neo from pMU388 and pLKm91.

Prolonged treatment over a period of 12–18 h of Bt8 protein with mosquito proteases resulted in further degradation towards a major 45 kDa polypeptide, which was essentially resistant to further proteolysis. This polypeptide sample however was not toxic anymore to mosquito larvae. Similarly an 18-hour treatment with trypsin and chymotrypsin yielded major polypeptides of 48 and 50 kDa respectively with a greatly reduced toxicity. The residual toxic activity still detected, probably is due to some non-digested 78 and 68 kDa polypeptides still present in these preparations (FIG. 3). The present data indicate that the Bt8 toxin can be degraded by proteolytic enzymes, including mosquito midgut proteases, towards similar polypeptide fragments of 68–80 kDa, which have retained full mosquitocidal activity.

In order to localize the region essential for toxicity on the Bt8 molecule we constructed deletion mutants of clone K514 (pMU188) using existing restriction enzyme sites in the Bt8 gene. Two 3' end deletion were generated: Bt8 AccI containing a 5' fragment of Bt8 up to the AccI site at bp position 2475 and Bt NdeI ending at the NdeI site at bp position 1820. This clone produced proteins of the expected size of 90 kDa and 67 kDa respectively, as determined in Western blotting (data not shown). When tested in insect assays, the Bt8 Δ AccI clone exhibited mosquitocidal activity while the shorter Bt8 NdeI clone was nontoxic. Thus the gene fragments encoding an active mosquitocidal polypeptide is localized in the N-terminal half of Bt8 on a fragment defined by clone Bt8Δ NdeI and clone Bt8ΔAccI (FIG. 1).

Materials and Methods for Examples 1 to 3

Purification of Cloned b.t. Toxin

The cell pellet from 1 liter saturated culture of E. coli (pMU388) was suspended in 100 ml of 50 mM Tris-HCl pH 7.9–50 mM EDTA—15% sucrose. The cell suspension was treated with lysozyme (100ug/ml) for 30 min at 0° C. then sonicated on ice until the cells were lysed completely.

The bacterial debris was removed by centrifugation at 10,000 rpm, 4° C. for 20 min. The pellet was resuspended in 50 ml of 1 MNaCl-1% Tritonx100–0.1 mM Phenylpethyl-sulfonyl fluoride (PMSF) and incubated at 0° C. for 30 min, then washed twice with 1 MNaCl-1% Tritonx100 and once with phosphate buffered saline (PBS). The Bt8 protein, present in this "final pellet", was solubilized in 5 ml extraction buffer (0.1 M $Na_2CO_3$ pH 9.5–0.2 M thioglycolate)at 37° C. for 2 Hrs. The solubilized protein was dialysed against PBS. Purity of protein was judged by SDS-PAGE. The concentration of protein was determined by using protein assay reagent (BioRad) according to the directions of the supplier.

Proteolytic Degradation of Bt8 Protein

All the experiments were performed at 37° C. Purified Bt8 protein (1 mg/ml), solubilized in PBS—0.5% $NH_4HCl_3$, was digested with trypsin or chymotrypsin (Sigma) 20:1 w/w. In case of mosquito gut protease, purified Bt8 protein (1 mg/ml) in PBS-1 M NaCl was digested with *A. aegypti* gut protease 1:10 w/w.

Gut protease preparation: 50 third instar *A. aegypti* larvae gut 1 first instar *M. secta* larvae midgut were disrupted in 1 ml of 50 mM $Na_2XL_3$ pH 9.5–10 mM DTT in a sonic bath. The debris was removed by centrifugation at 10,000 rpm for 10 min. Protein concentration of the supernatant was estimated. The supernatant was stored in aliquots at 20° C.

Bioassay on Mosquito Larvae

A total of tested suspension 1 ml was placed in each wall of a 12 mm diameter microtiter plate. Larvae of *A. aegypti* or Anopheles were added. Mortality was scored at 30° C. 24 hours. For acid precipitated samples, solubilized protein was precipitated by adding 1/10 vol. of 12% citric acid. Precipitated protein was pelleted by centrifugation and resuspended in distilled water.

Immunological Assay

Antisera against B.t. protein(s) were obtained by subcutaneous injection of the protein(s) into New Zealand White rabbits. Specificity of antisera was confirmed by Western blotting using alkaline phosphatase conjugated anti-rabbit immunoglobulin (Sigma) to detect bound antibody according to the directions of the supplier.

Enzyme linked Immunosorbent Assay (ELISA) was performed to the method of Engval and Pesce. (Scand. Immunol. Suppl., 7, 1978).

Amino Acid Sequencing

Amino-terminal sequences of Bt8 protein were determined by using a gas-phase sequenator (applied Biosystems Inc.

USA) operated essentially according to Hewick et al, cited above.

DNA Manipulations and Computer Analysis

Restriction endonuclease enzymes were used as described by the supplier (New England BioLabs, Inc.; and Bethesda Research Laboratories Inc.). Restriction mapping and subcloning were performed according to Maniatis et al (Molecular Cloning, A Laboratory Manual, Cold Spring Harbour Laboratory, New York). DNA sequences were determined by the Maxam and Gilbert method (Methods Enzymol., 65 (1), 497–559 1980). Protein hydropathy was computed by the method of Kyte and Doolittle (J. Mol. Biol. 157, 105–132, 1982).

TABLE 1

The mosquitocidal activity of plasmid-harboring *E. coli* K514 to 10 third instar larvae of *A. aegypti*

| *E. coli* K514 clone[a] | Mosquitocidal activity (dead/total) |
|---|---|
| pUC12 | 0/10 |
| pMU388 | 10/10[b] |
| bt8 AccI | 8/10 |
| bt8 NdeI | 0/10 |

[a]Cells from 4 ml culture at $O.D._{600}$ 0.7 were harvested by centrifugation, and resuspended in 1 ml water.
[b]Toxicity tests on newly hatched larvae with purified, citric acid-precipitated Bt8 protein from clone pMU388 gave LD50's of 532 ng/ml for Anopheles sp and 22 ng/ml for *Aedes aegypti*.

TABLE 2

Toxicity of B.t.i and B.t. berliner crystal proteins on *M. Sexta* 1st instar larvae and *Aedes aegypti* 2nd instar larvae.

| B.t. toxin protein | *A. aegypti* LC50 (a) (ng/ml) | *M. sexta* LC50 (ng/cm2) |
|---|---|---|
| B.t.i native crystals | 5 | >1500 |
| B.t.i solubilized crystals | 50 | >1500 |
| Bt8, solubilized (from *E. coli*) | 100 | >1500 |
| Bt8, precipitate (in *E. coli*) | 5 | n.t. |
| B.t. berliner native crystals | >100 | 80 |
| B.t. berliner solubilized crystals | >100 | 7.5 |
| Bt2, solubilized | >100 | 6 |

(a) LC50: Toxin concentration giving 50% mortality, determined after 24 h for *A. aegypti* and after 5 days for *M. sexta* larvae.
(b) n.t.: not tested

EXAMPLE 4

Construction of the Bt8: Neo Fusion Gene

It was demonstrated in Example 4 that a fragment of the coding sequence of gene Bt8 (the 5' half of the gene up to bp position 2322 of the coding sequence, defined by an AccI site) encodes a toxic polypeptide. This fragment was fused to the intact neo gene of Tn5 on pBR322 (Reiss et al., EMBO J. 1984).

a. Construction of pBIN10 Comprising a Bt8:neo Fusion Gene (FIGS. 3–4)

pLKm91has previously been described (Eur. patent appl. No. 85300291.1)

pMU388 was described in the thesis of Chanun Angsuthanasombt, Molecular cloning and expression of A endotoxin gene of *Bacillus thuringiensis* var. *israelensis* in *Escherichia coli,* Mahidol University, 1985, Bangkok, Thailand.

pLKm91DNA, treated with HindIII, the Klenow fragment of DNA polymerase (Klenow), BamHI and cip, was ligated to a 2.4 kb fragment obtained by treatment of pMU388 DNA with AccI, Klenow and BamHI, and recovered from a preparative agarose gel. The recombinant clones were isolated by selection on Ampicillin (100 ug/ml) and screening for kanamycin (20 ug/ml) resistance.

b. Characteristics of the Fusion Protein Expressed in *E. coli*

The fusion gene Bt8:neo behind the PL promoter in plasmid construction pBIN10 was expressed in *E. coli,* to study the properties of the encoded fusion protein. *E. coli* K12 Hl trp transformed with pBIN10 was analyzed in SDS-PAGE and in Western blotting. Coomassie staining of the complete bacterial extract in SDS-PAGE showed the presence of a new protein band having an apparent molecular weight corresponding to the expected size of the fusion protein (approximately 110 Kda). The protein could also be visualized in Western blotting using either anti-Bti crystal serum, anti-Bt8, or anti-NPTII serum. Again the positively reacting band showed the expected size of the fusion protein. The protein is quite stable in *E. coli* since almost no degradation products were detected (bands of lower M.W.).

The *E. coli* clone K12ΔHΔtrp containing pBIN10 was indeed resistant to kanamycin. Bacteria were able to grow on 400 ug/ml Km (at 28° C.). NPTII activity of the fusion protein was evaluated using an NPTII assay as described (Reiss et al., Gene, 30, p. 217, 1984). A cell extract of the *E. coli* clone expressing the Bt8:NPTII protein was run on gel in nondenaturing conditions, in parallel with an extract from an *E. coli* clone producing the wild type NPTII. Cell extracts were prepared as follows. The *E. coli* clones were grown during about 4 hours at 38° C. in 20 ml cultures (containing LB medium), centrifuged and resuspended in 1 ml TES buffer, sonicated twice at 50 watts in Labsonic 1510 and centrifuged for 30 minutes at 15 rmp; the supernatant was used in the experiment. The NPTII-specific activity of the proteins was determined by in situ phosphorylation of kanamycin, using 32p-ATP (Reiss et al., 1984, Gene 30, 217–223). The results indicated that the Bt8:NPTII protein exhibited specific NPTII activity. *E. coli* clone K12ΔH1Δtrp (pBTN10) was analyzed for expression of functional toxin in an insect assay. Addition of the *E. coli* cells to the water killed *Aedes aegypti* larvae within 48 hours (Table 3). Control *E. coli* K12ΔH1Δtrp, not containing pBIN10, had no effect. Thus the Bt8:NPTII protein expresses both mosquito toxicity and NPTII enzyme activity.

Based on their results a vector system could be developed for transfer of foreign genes such as the B.t. genes into Cyanobacteria.

EXAMPLE 5

Transformation of Cyanobacteria a. The vector system for transformation of Cyanobacteria Vectors for transformation of Cyanobacteria are plasmids or linear DNA comprising bacterial antibiotic resistance genes linked to fragments of Synchocystis 6803 NDA. These plasmids will be referred to as "donor" DNA molecules", Cyanobacterial cells mixed with donor DNA in transformation experiments are designated as "recipient cells". Each donor molecule consists of a fragment of Synechocystis 6803 cloned in an *E. coli* vector. The vector contains an ampicillin (Ap) resistance gene, (for selection in *E. coli*), whereas a kanamycin (Km) resistance gene (for selection of the transformed Cyanobacteria) is inserted into the Cyanobacterial DNA.

By way of example, we mention the donor plasmid pKW1188 (McIntosh, Lee, in Molecular Form and Function of the Plant Genome; Plenum Press, New York, pp. 335–346 (1985)). It contains a fragment of Synechocystis 6803 chromosomal DNA cloned into *E. coli* PKW1159 and containing an inserted Km resistance gene from Tn903 (FIG. 5). Using this pKW1188 donor plasmid as a vector to transfer the Km resistance gene to Synechocystis, Km resistant Cyanobacteria can be obtained at frequencies lower than 1 in 1000.

b. Method to Transform Synechocystis

Synechocystis 6803 (Rippka et al., J. Gen. Microbiol III, 1–61, 1979) was obtained from the American Type Culture Collection. As determined by counting cells in a Petroff-Hauser chamber, an optical density ($A_{730}$) of 1.2 corresponds to about $10^8$ cells per ml. Cells were grown in BG-11 medium (Rippka et al., 1979) cited above at 34° C. in a light flux of 1500 lux from warm white fluorescent tubes.

Liquid cultures were perfused with air at 50–150 ml/min/100 ml culture volume. The air was moistened by bubbling through a solution of one percent $CuSO_4$ and sterilized by passage through two filters (Gelman no. 12123 and no. 4210, Ann Arbor, Mich.). Under these conditions, a minimum of 8 h was required for the density of the culture to double. Solid medium was prepared by mixing an autoclaved solution of 3% Difco Bacto Agar (Detroit, Mich.) with an equal volume of 2×BG-11 salts (Allen, 1968). *E. coli* HB101 (Bolivar and Backman, Methods Enzymol. 68, 309–326, 1979) was used in all DNA constructions; it was cultivated in LB medium and cells were prepared for transformation by treatment with $CaCl_2$ (Maniatis et al, 1982, cited above); to select for transformants, kanamycin was used at 25 ug/ml, ampicillin at 50 ug/ml.

To prepare competent cells, an actively-grown culture (A730–0.3 to 2.0) of Synechocystis 6803 was diluted to A730=0.5 to 0.10 in fresh BG-11 medium and was grown overnight until A730 was between 0.2 and 0.4. The cells were harvested by centrifugation at room temperature, were suspended in BG-11 medium at A730=2.5 ($2\times10^8$ cells per ml), and were used immediately for transformation. Cells were mixed with donor DNA and were incubated in a glass tube under standard growth conditions, except that the cell suspension was not bubbled with air. We refer to this mixture of cells and DNA as a "transformation mixture". The DNA, in 10 mM Tris-HCl, pH 7.5, 0.1 mM EDTA, was added in a volume not greater than 2 percent of the volume of the cell suspension. After incubation for at least 2 h, 0.1 ml samples of the transformation mixture were spread on membrane filters (MF Membrane, 0.45 um, from Nuclepore, Pleassanton, CA) resting on agar medium in polystyrene petri plates. The plates were incubated for 18 to 20 h and the filters were transferred to agar medium containing the appropriate antibiotics (kanamycin at 5 ug per ml; ampicillin at 0.3 ug per ml). Colonies of transformed cells could be visualized within 4 days.

EXAMPLE 6

1. Creation of Plasmid pBIK1188 (FIG. 6)

Recombinant plasmid pBIK1188 was created starting from plasmids pKW1188 (McIntosh et al., 1985 cited above) and pBIN10 (see Example 5), using the following experimental protocols:

1. pKW1188 is
   - cut with HindIII and Klenow treated
   - cut with SalI so that part of the neo gene is cut out and a linear fragment of ±5.7 kb is obtained with one blunt end and one sticky end (from SalI)
2. pBIN10 is
   - cut with SspI and SalI so that a linear fragment of ±4.2 kb, containing the Bt8:neo gene behind the Lambda phage PL promoter, is obtained.
3. Ligation of fragments obtained in 1) and 2) results in the recombinant plasmid pBIK1188. *E. coli* K51: cells transformed with the ligation mixture are selected on Ap 100 ug/ml and Km 50 ug/ml, to select for clones containing plasmids pBIK1188.

Plasmid p BIK1188 contains:

A 5' fragment of the neo gene from Tn903 which was originally present on pKW1188 (up to the HindIII site). This is not a functional $Km^R$ gene any more.

The Bt8:neo fusion gene behind the PL promoter

Synechocystis DNA fragments flanking the fusion gene

The $Ap^R$ marker gene.

Thus plasmid pBIK1188 contains the Bt8:neo gene behind a promoter which is functional in Cyanobacteria (the PL promoter induces expression in Cyanobacteria) (Friedberg and Seijffers, *Mol. Gen. Genet.* (1986) 203 p. 505–510). It can be used as donor plasmid to transfer and express this gene into Cyanobacteria.

2. Selection of Transformed Cyanobacteria Clones Containing the Bt8:Neo Gene

Plasmid pBIK1188 can function as a "donor" plasmid to transfer the Bt8:neo gene into the chromosomal DNA of Synechocystis. Since the $Km^R$ of the Bt8:neo fusion is a functional $Km^R$ resistance gene, selection for $Km^R$ will allow to select for transformed clones of Synechocystis, containing this Bt8:neo fusion gene.

Synechocystis 6803 cells were transformed with the "donor" plasmid and transformed clones were to be selected on medium containing 5 ug/ml Km. Several hundred transformed clones were obtained in one experiment. Two clones selected at random were used for further characterization: clone 20 and clone 43.
3. Characteristics of Transformed Cyanobacteria
   1 Southern blotting confirmed the presence of the Bt8:neo gene in clones 20 and 43:
      Cyanobacterium clone 20 and clone 43 chromosomal DNA was purified and digested with BamHI or EcoRI restriction enzymes. Southern blotting of the digested DNA showed that the 1.8 kb XbaI fragment from 5' end of the Bt8 toxin gene, used as probe, hybridized with a 3.4 kb EcoRI and with a 3.6 kb BamHI fragment of the Cyanobacterium chromosomal DNA. This result indicates that the Bt8:neo fusion gene did integrate into the chromosome of Cyanobacterium clones 20 and 43.
   2. Expression of the recombinant protein Bt8:NPTII in clones 20 and 43 was analyzed using immunological assays. Western blotting showed that indeed these clones expressed the Bt8:NPTII fusion protein:
      Total cell lysate of the Cyanobacterium clones was separated on SDS-PAGE, the protein were transferred onto nitrocellular paper and probed with either a rabbit anti Bt8 serum or a rabbit anti-NPTII serum. The results showed the presence in clones 20 and 43 of a new polypeptide with apparent MW of 110.000 Da which reacted with both anti-Bt8 and anti-NPTII antibodies. This protein was not detected in untransformed Synechocystis cells. Thus clones 20 and 43 express the Bt8:NPTII fusion protein.

EXAMPLE 7

Figure 7:
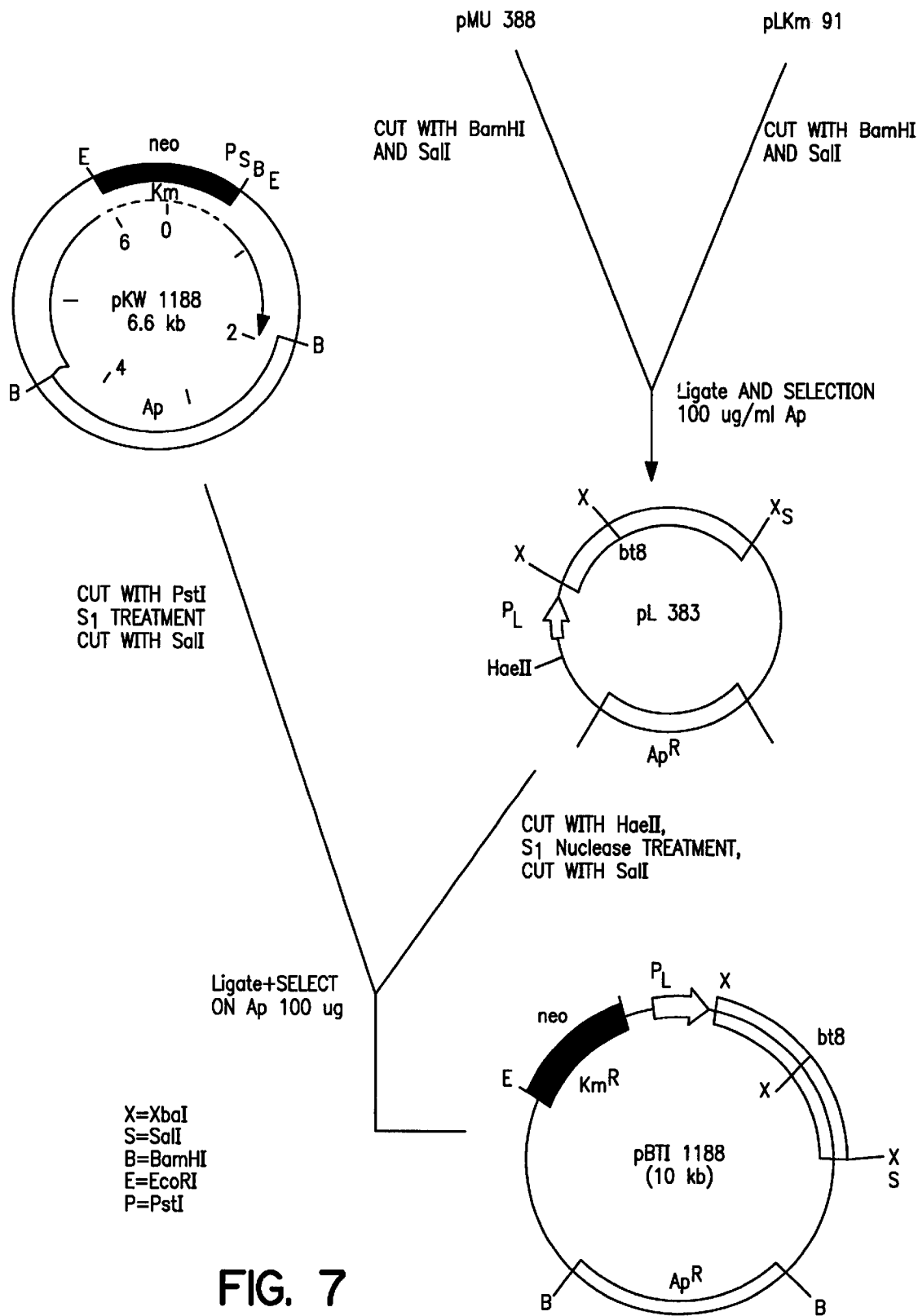
FIG. 7 shows the construction of pBIT 1188.
Figure 7A:
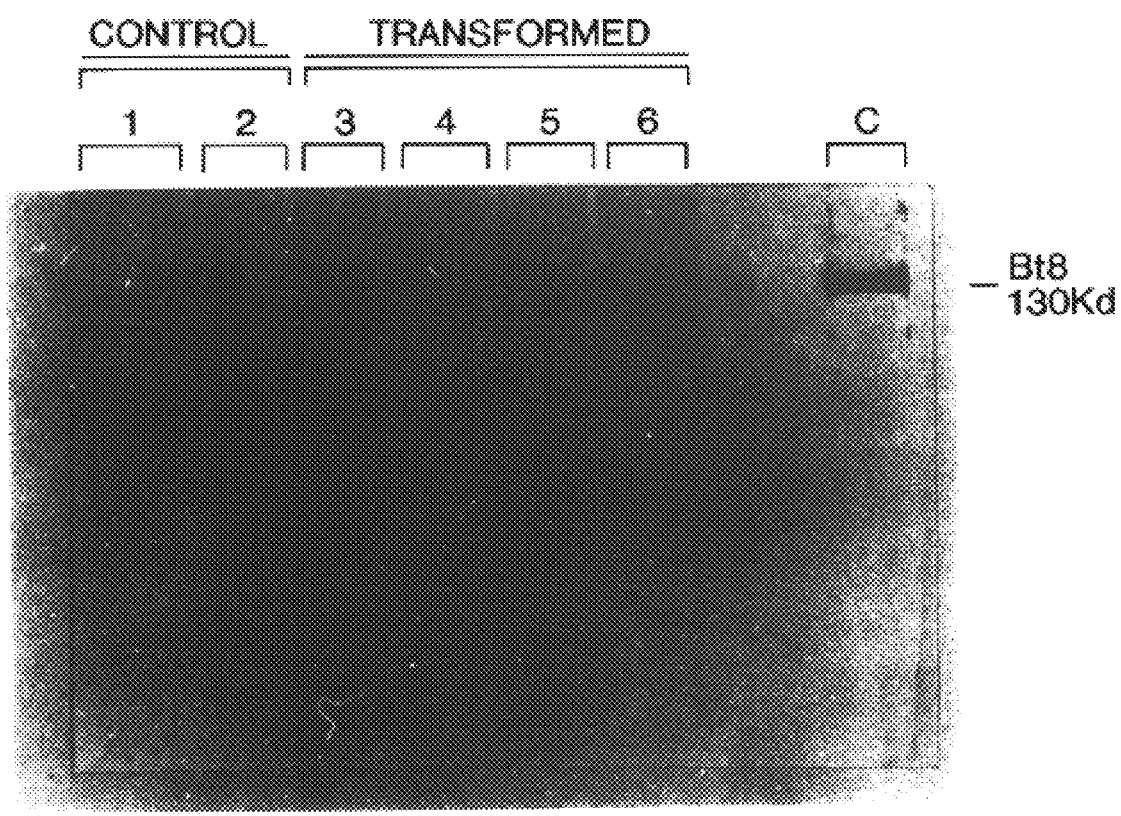
FIG. 7A shows the western blot of Bt8 expression in Synechocystis.
Figure 8:
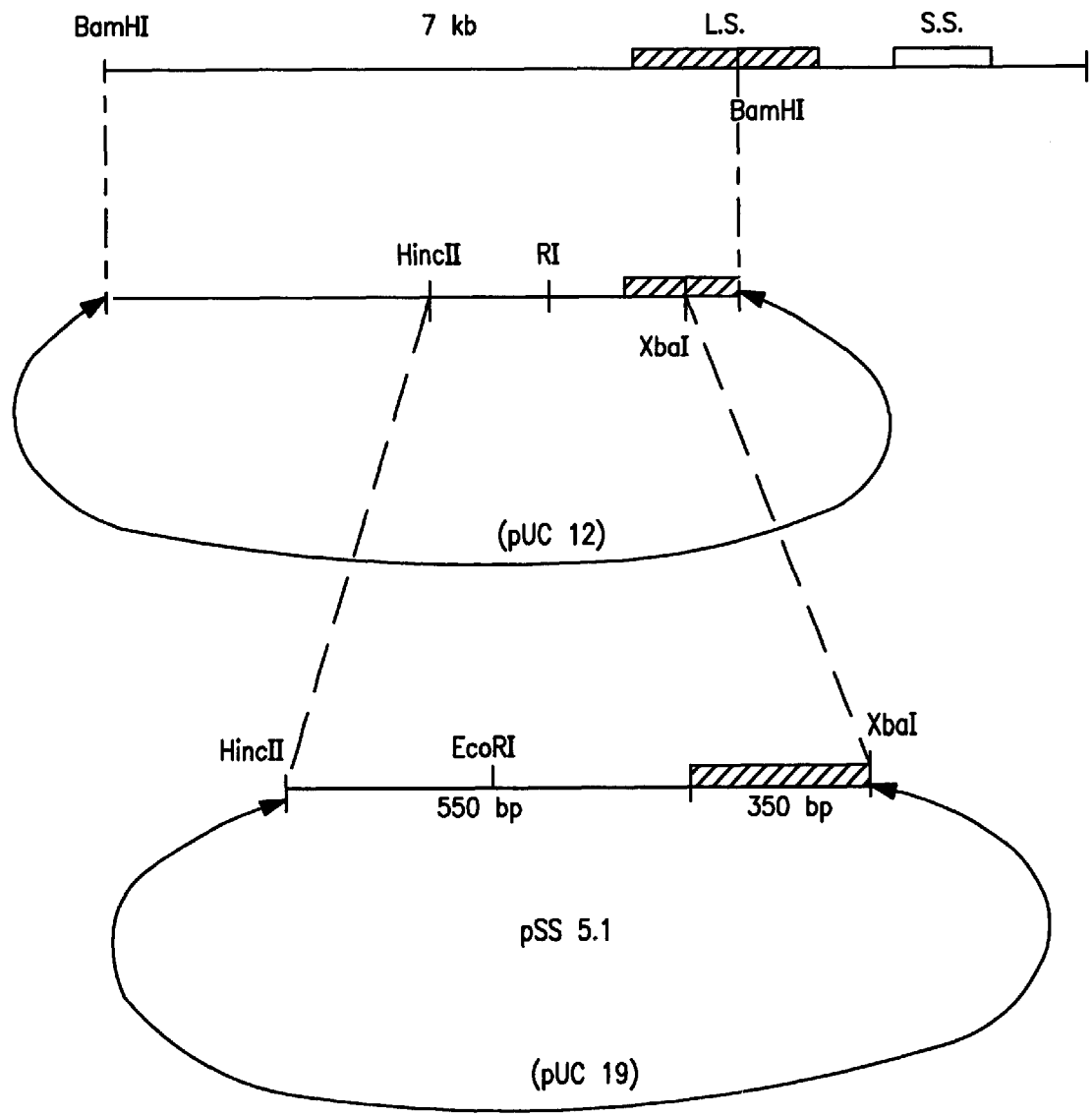
FIG. 8 Shows the isolation of a DNA fragment from Synechocystis 6803 comprising the promoter sequence directing expression of the rubisco operon.

1. Creation of Plasmid pBTI1188 (FIG. 7)
   To obtain pBTI1188, the complete Bt8 toxin gene from plasmid pMU388 is placed behind the Lambda $P_L$ promoter and cloned into pKW1188, next to the $Km^R$ gene (FIG. 6). The intact $Km^R$ gene of pKW1188 is still present and can be used as a selection marker for screening transformants.
1.1 Construction of pL383 Containing the Intact Bt8 Gene Behind the PL Promoter
   1. pMU388:
   cut with BamHI and SalI
   a linear DNA fragment of ±3.6 kb with
   2 stick ends containing the Bt8 gene is obtained.
   2. pLKm91:
   cut with BamHI and SalI
   a linear ±2.9 kb DNA fragment is obtained, comprising the PL promoter and $Ap^R$ gene.
   3. Ligation of the fragments obtained in 1. and 2.
   Ligation mixture is transformed in K514 E. coli and transformed clones are selected for $Ap^R$ (100 ug/ml).
1.2 Construction of pBTI1188
   1.1383:
   cut with HaeII (+Sl treatment) and SalI
   a linear ±4 kb DNA fragment containing Bt8 behind PL
   2. pKW1188
   cut with PstI+Sl treatment and cut with SalI
   a 6.6 kb linear vector fragment is obtained
   3. Ligate the fragments obtained in 1. and 2. and select transformed E. coli on 100 ug/ml Ap.
   Plasmid pBTI1188 contains:
   the Bt8 gene behind the PL promoter
   a functional neo gene
   flanking Synechocystis chromosomal DNA sequences
   $Ap^R$ marker gene
2. Transformation of Cyanobacteria with pBTI1188 and Selection of Transformed Clones
   Plasmid pBTI1188 has been used as a donor plasmid to transfer the Bt8 into Synechocystis 6803 cells. Transformed 6803 clones were selected on medium containing 5 ug/ml of Km. Several hundreds of transformed colonies were obtained per 1 ug of DNA. Results on Western blot are shown in FIG. 7A.

EXAMPLE 8

Figure 9:
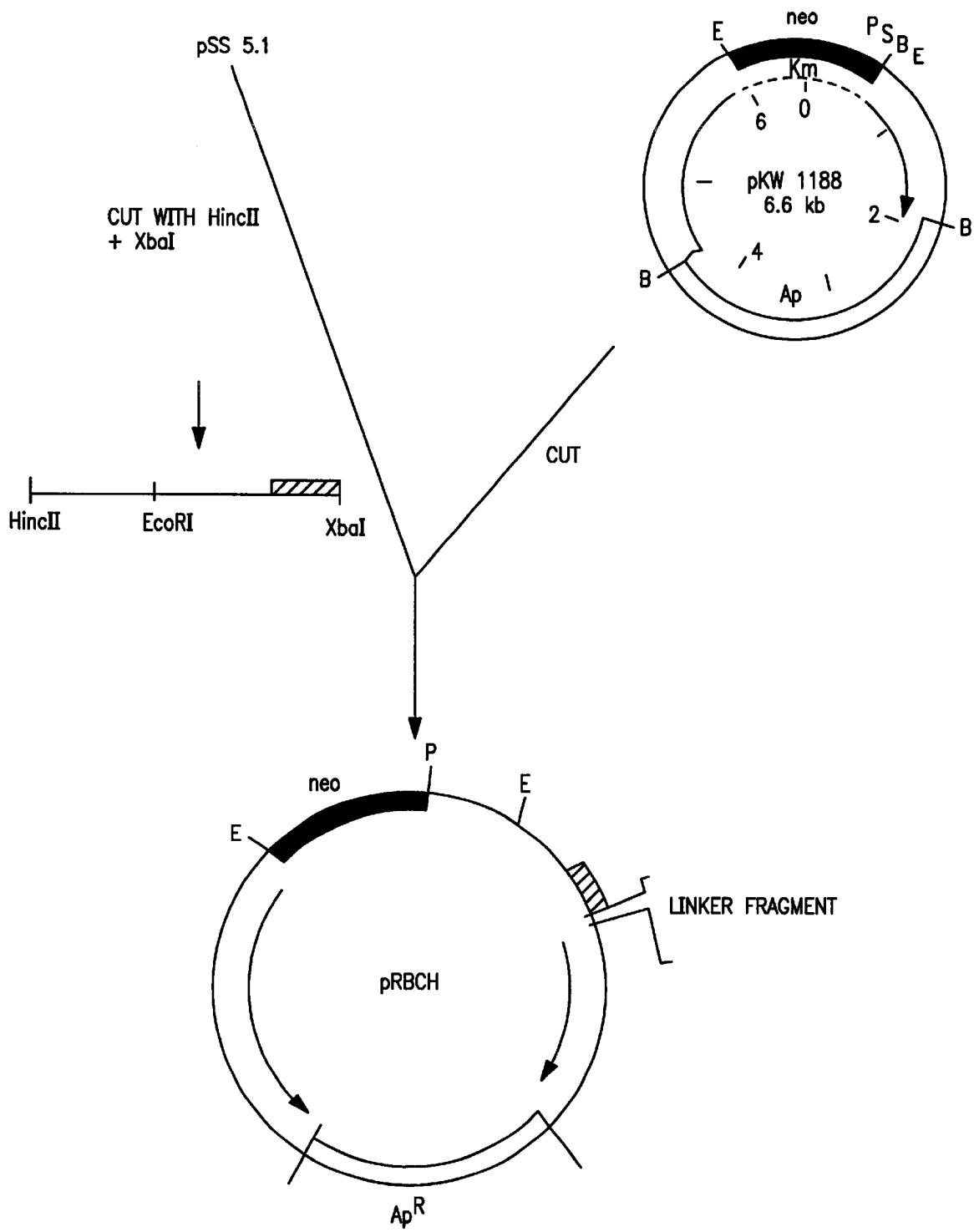
FIG. 9 Shows the construction of plasmid pRBC4
Figure 10:
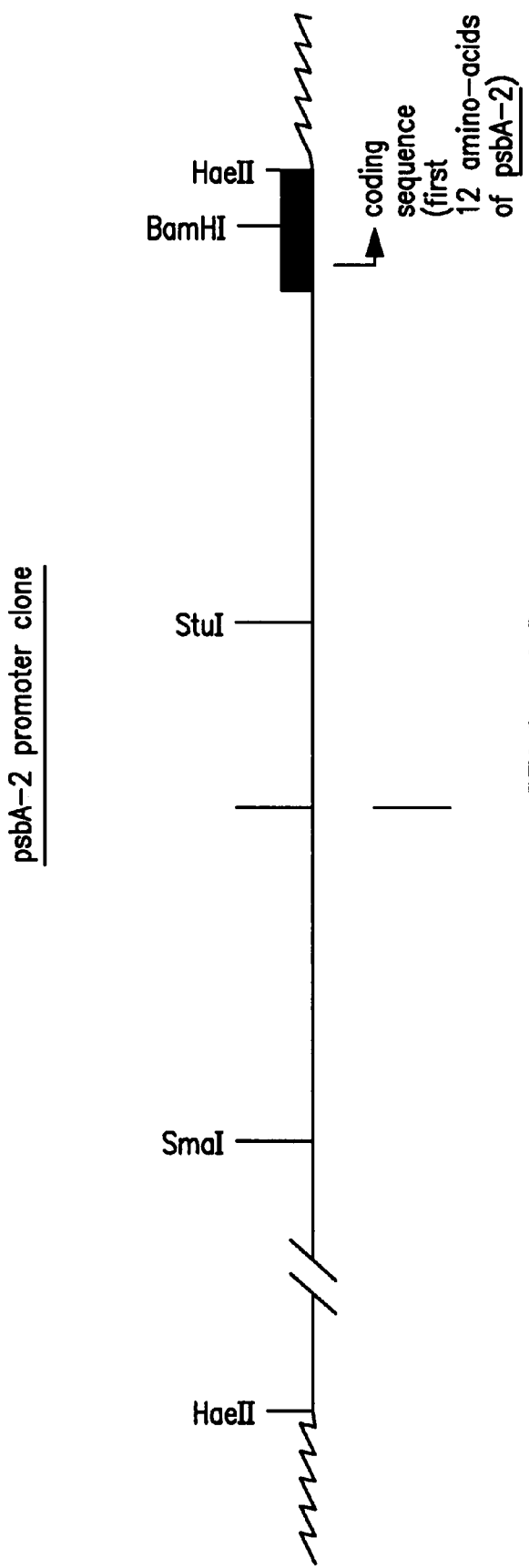
FIG. 10 shows a restriction enzyme map of Hae II insert of the promoter region of psbA-2 in Sma I of pUC19 as shown in FIG. 15.
Figure 11:
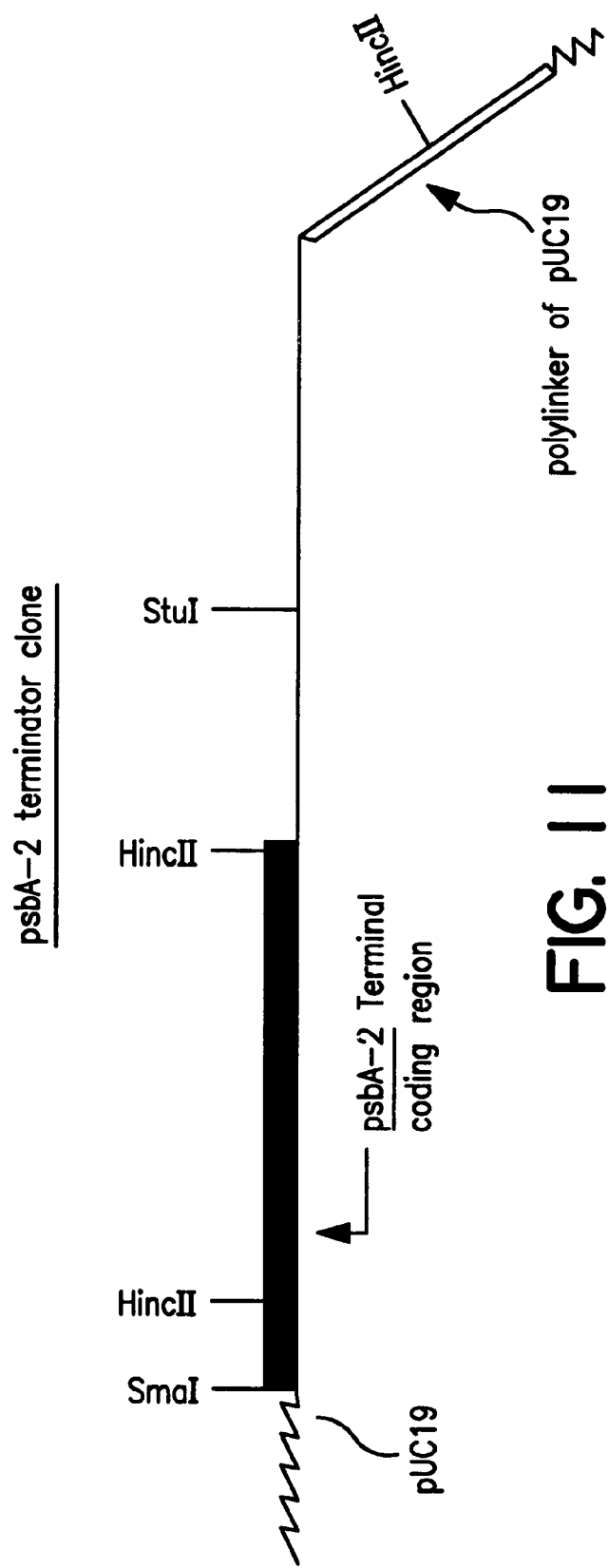
FIG. 11 shows a restriction enzyme map of Hae II clone of the termination region of psbA-2 in Sma I of pUC19 as shown in FIG. 15.

B.t. derived toxin genes are placed behind a strong promoter yielding high expression in Cyanobacteria such as f.e., the Synechocystis 6803 promoter for the rubisco operon.
1. Creation of a Vector Comprising the B.t. Genes Behind the Synechocystis 6803 Promoter for the Rubisco Operon
   The rubisco operon of Anabaena has been cloned and characterized (Curtis & Haselkern, PNAS, 80, 1835–1839, 1983 and Nierzwicki-Bauer et al., PNAS, 81, 5961–5965, 1984). Using part of this sequence as probe, a DNA fragment comprising, presumably, the promoter and part of the coding sequence of the large subunit of rubisco (L.S.) has been cloned from Synechocystis into E. coli. From this ±7 Kb BamHI fragment a ±900 bp HincII-XbaI fragment has been subcloned into pUC19, generating plasmid pSS 5.1 (FIG. 9). This fragment contains ±550 bp of 5' upstream sequence and ±350 bp of the L.S. coding region.
   This fragment was recombined into expression vector pKW1188 to create a new plasmid called pRBC4 (FIG. 9). Just behind the coding sequence of L.S., a linker fragment containing a number of cloning sites, was inserted.
   Therefore pRBC4 contains:
   all elements present on pKW1188
   a 5' upstream sequence of the Synechocystis L.S. gene, presumably comprising the promoter sequence for the rubisco operon
   part of the L.S. coding sequence
   a linker fragment containing suitable, restriction enzyme sites for cloning (XbaI, EcoRV, SalI, BamHI, EcoRI)
   B.t. genes (Bt8 and Bt8:neo) have been inserted in the cloning site of pRBC4. The obtained recombinant plasmids called pRFB 1188 were used to transform Synechocystis 6803 and to transfer the B.t. genes inserted behind a promoter fragment which induces high level expression of these genes.

TABLE 3

Mosquitocidal activity of E. coli clones harboring bt8 derived toxin genes (number of dead 2nd instar Aedes aegypti (larvae).

| E. coli | No | | Number of dead/viable larvae | |
|---|---|---|---|---|
| clone | 108 cells/ml | Toxin | 20 h | 48 h |
| Control pUC12 | 7 | — | 0/10 | 0/10 |
|  | 28 |  | 0/10 | 0/10 |
| pMU388 | 7 | Bt8 | 4/10 | 6/10 |
|  | 28 |  | 10/10 | 10/10 |
| pLKm9l | 7 | — | 0/10 | 0/10 |
|  | 28 | 0/10 | 0/10 |  |
| pBIN10 | 7 | Bt8:NPTII | 3/10 | 9/10 |
|  | 28 |  | 3/10 | 9/10 |

EXAMPLE 9

Improvement of the Expression of the Bt8-Gene in Cyanobacteria Using Promoter From New Genes According to the strategy as described under Example 8, new constructs were made with the Cyanobacteria shuttle/ integration vector pKW1188, using new strong promoters, especially the promoters controlling the expression of the psbA genes, for the expression of Bt endotoxins in Cyanobacteria.

The psbA gene family represents a class of genes encoding a photosynthetic polypeptide, called D1, which is involved in the Photosystem II (PSII) in blue-green algae and in higher plants. The different psbA genes constituting the psbA gene family are nearly identical (Jansson et al., (1987) Plant Physiol. 85, 1021–1025). In general, this class of genes are highly transcribed because of the rapid turnover of the polypeptide D1 and thus requires a strong promoter of transcription.

In relation to the present invention, the promoters of the psbA genes from Synechocystis 6803, more specifically the psbA-2 gene and its promoter are used to highly express Bt genes in Synechocystis and in Cyanobacteria in general. The Bt gene to be expressed can be used either in its complete version of 3680 bp, or in its truncated version of 1860–2475 bp, provided the gene used encodes a protein with sufficient toxicity against mosquito larvae. The concerned Bt gene can be fused either behind the start codon of the psbA-2 gene, making use of a restriction site available at that position or created through site-directed-mutagenesis, or by fusing the Bt8 gene in frame to a part of the coding sequence of the psbA gene. On the other hand, the transcription and termination sequences of the psbA gene are also employed without a translational fusion, since this may ensure the correct termination of foreign genes in Cyanobacteria.

A detailed description of an example of the "in-frame" fusion of psbA-2 with Bt8 is given below and illustrated with FIGS. 10 to 15.

The following steps were undertaken:

1. One Hae II fragment (1.8 kb) containing respectively the psbA-2 promoter sequence (FIG. 10) and one HincII fragment (2.2 kb) containing the psbA-2 termination sequences (FIG. 11) were sub-cloned from a EMBL 3 phage library in pUC19 (Yannisch-Perron et al., (1985) Gene 33, 103–119) according to Jansson et al, (1987), Plant Physiol. 85, 1021–1025.

Figure 12:
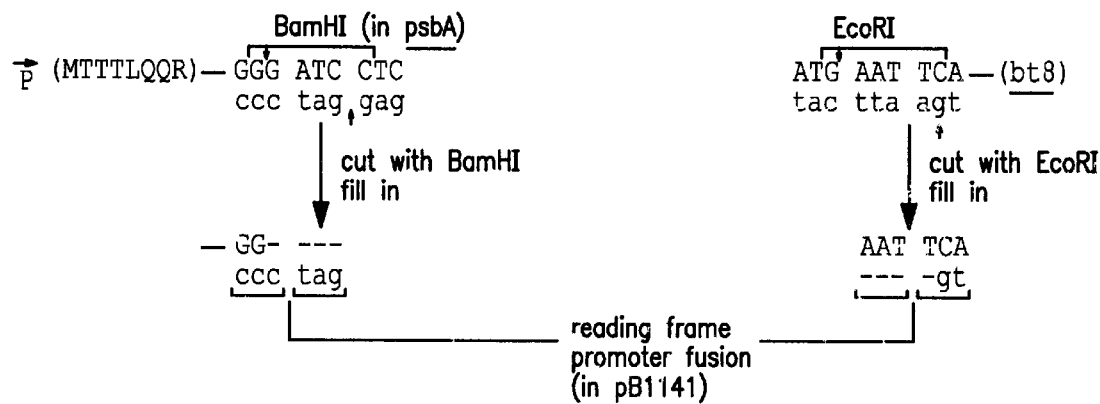
FIG. 12 shows fusion of the Bam HI site of the psbA-2 promoter gene as shown in FIG. 10 with the Eco RI site of Bt8 gene shown in FIG. 1.
Figure 15:
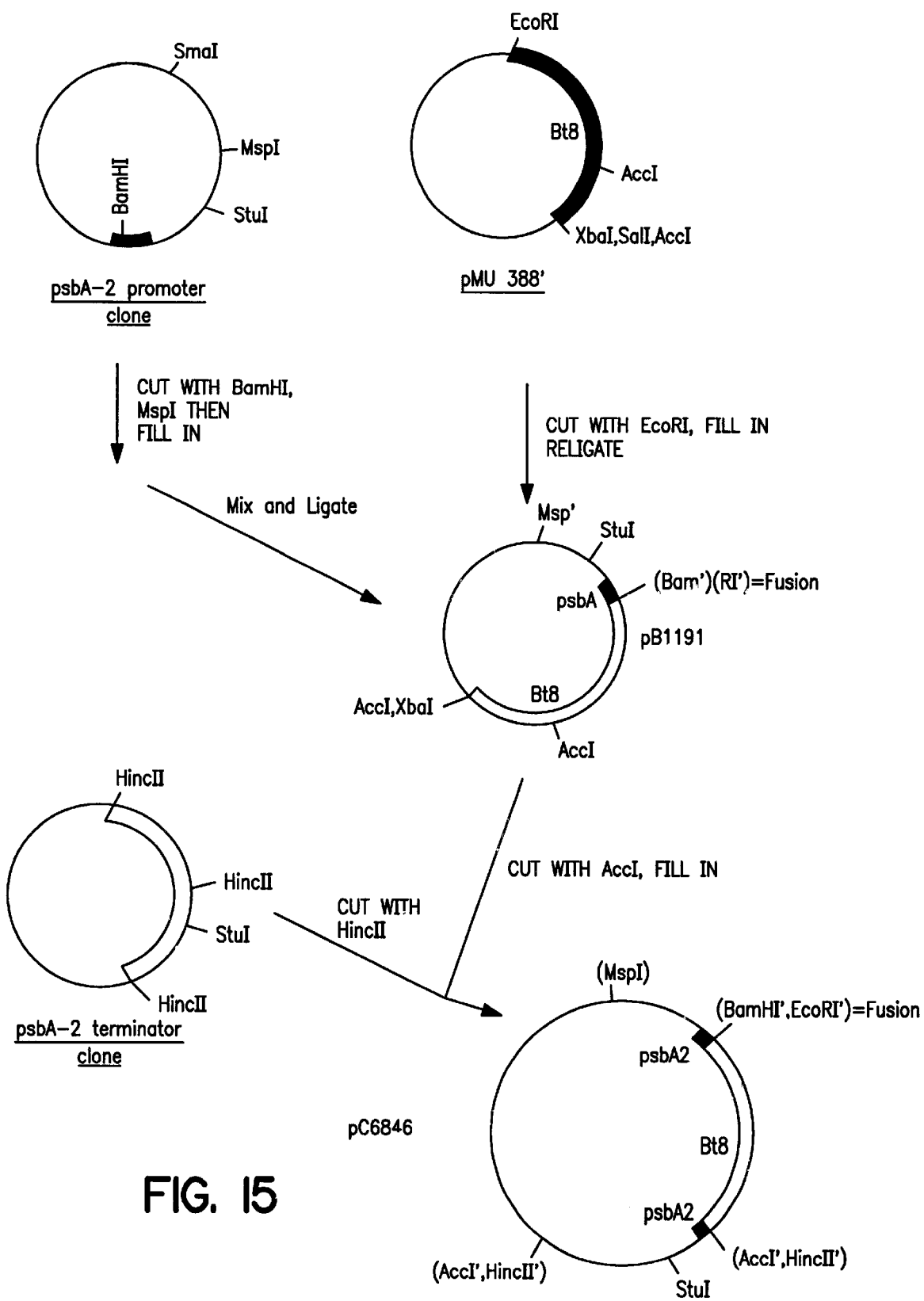
FIG. 15 shows cloning of the Stu I DNA fragment of FIG. 14 in the SalI site of pkWl188.

2. The psbA-2 promoter fragment cloned in pUC19 is cut at the BamHI site, which is situated in the coding sequence of the psbA-2 gene (as shown in FIG. 12) treated with Klenow polymerase, and fused to Bt8 at the Klenow treated Eco RI site of pMU388, being situated at the start of the coding sequence of the Bt8 gene. Both fragments are ligated as shown in FIG. 12 and the missing bases were filled in. This resulted in the construction of pB1141, (FIGS. 12, 15).

Figure 13:
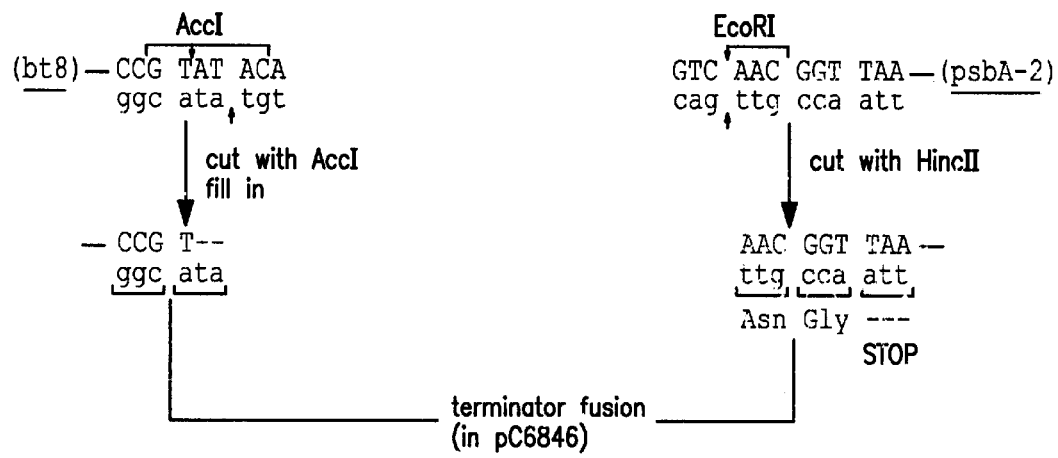
FIG. 13 shows fusion of the AccI site of Bt8 as shown in FIG. 1 with the Hinc II site in front of the psbA-2 termination sequence is cloned as shown in FIG. 11.
Figure 14:
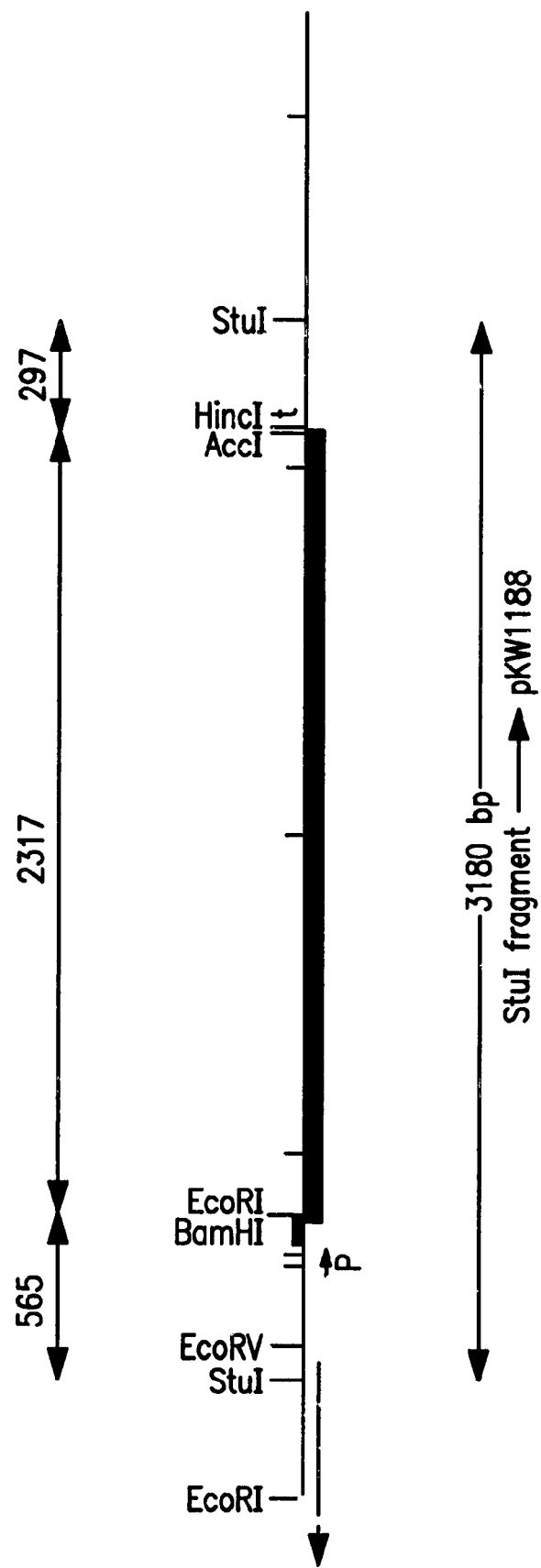
FIG. 14 shows an in-frame fused psbA-2 promoter gene, psbA-2 termination gene, Bt8 truncated gene, which is cloned into the pMU 388 and also shows the Stu I sites.

3. pB1141 is digested with AccI, cutting the unique AccI site of the Bt8 gene, providing the truncated Bt8 gene from 2478 bp (as shown in FIG. 1), and is ligated with the psbA-2 gene cloned in pUS19 which has been digested with HincII. This results in the construction of pC6846 (FIGS. 13, 15). In this plasmid the psbA-2 promoter, the truncated Bt gene and the psbA-2 terminator gene are fused in frame together and can be cut out as a single Stu I DNA fragment, as illustrated in FIG. 14.

Figure 14A:
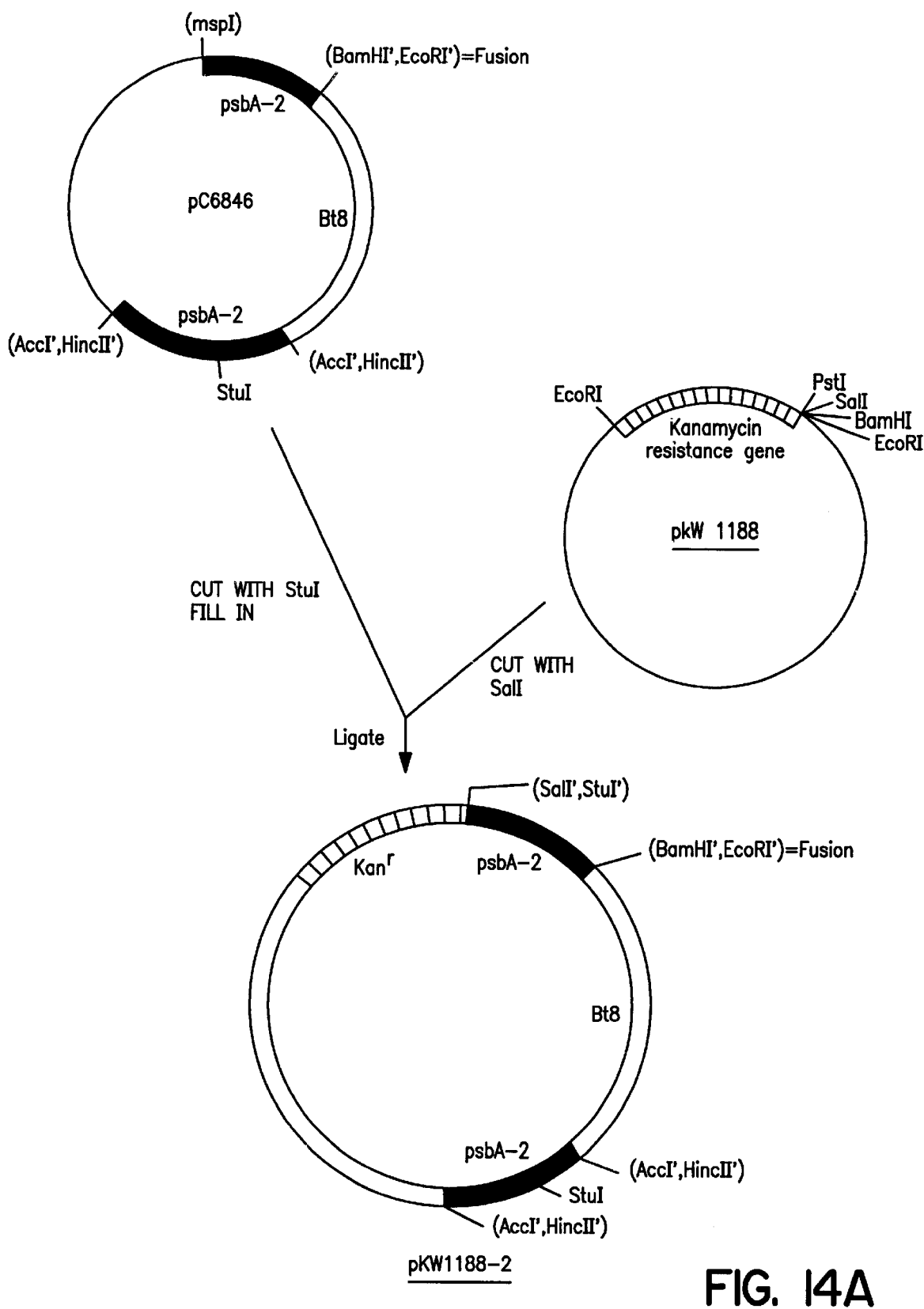
FIG. 14A shows the construction of pKW1188–2 by cloning of the StuI fragment of pC6846 into the SalI site of pKW1188.

4. The Stu I DNA fragment from pC6846 can be cloned out into the Sal I site of any shuttle/integration vector for Synechocystis, for example pKW1188, as described in Example 8 and in McIntosh et al., 1985 (cited above). The resulting plasmid is called pKW1188–2. The construction of the plasmid is shown in FIG. 14A.

5. Finally, Synechocystis can be transformed with this recombinant plasmid as described in Example 5, and transformants are screened for Kanamycin resistance.

EXAMPLE 10

Simultaneous Expression of Bt8 and the 27 Kda Toxin of B.t. isrealensis in Synechocystis Wu and Chang (1985, FEBS Lett. 190, 232–236) demonstrated a synergism in the mosquitocidal activity of the 27 kDa and the 65 kDa proteins resp. the 130 kDa proteins, purified from B.t israelensis.

In order to obtain improved insecticidal activity of transformed Cyanobacteria for the control of mosquito larvae, transformation constructions were made in which the Bt8 gene and the gene encoding the 27 kDa toxin are combined.

Therefore, the following steps were undertaken:

A 880 bp HaeIII—TaqI fragment containing a 27 kDa toxin gene was cloned from Bt. israelensis according to Ward and Ellar (1986, J. Mol. Biol. 191, 1–11). This fragment was cloned in the pUC19-psbA-2 promoter vector between the Klenow polymerase treated TaqI site, situated at position 2029 behind the psbA-2 promoter sequences and the HincII site (position 1053) at the 3' end of the psbA-2 gene as illustrated in FIG. 16. The 1692 bp Stu I fragment containing the psbA-2 promoter, the 27 kDa toxin gene and the 3' end of the psbA-2 was treated with Klenow polymerase and moved into the Bam HI site of pKW1188–2. This results finally in pKW1188–3.

Synechocystis 6803 was transformed as described in Example 5. The expression of the different Bt genes are analyzed in Western blotting, with rabbit antisera raised against Bt israelensis crystals.

It is clear that other combinations with other Bt entoxin genes (see Example 12) can be made, in order to improve the toxic activity of the transformants, to broaden the insecticidal spectrum of the transformants, and/or to prevent the development of resistance with the targeted mosquito larvae.

EXAMPLE 11

Construction of Herbicide Resistant Cyanobacteria Expressing the Bt8 Gene

In the view of using the transformed Cyanobacteria in natural habitats of mosquito larvae, it is important to provide to the transformed blue-green algae an additional characteristic which renders it more competitive in surviving in that habitat, compared with non-transformed blue-green algae naturally present in said habitat. So the present invention deals with the insertion and the expression of a gene, the so called bar gene, which inhibits the herbicidal effects of Bialaphos and related compounds (as described in the European patent application 87400521), in the genome of Cyanobacteria. This inhibition is due to a phosphinotricine acetyl transferase activity (PAT) of the bar gene product.

Expression of Bar-gene in Synechocystis 6803

For this purpose the psbA promoter gene from Nicotiana tabaccum was used (Sugita, M. and Sugiura, M. (1984)Mol. Gen. Genet. 195, 308–313). Since this promoter is active in the plant chloroplasts, it is presumed to function in prokaryotic cells such as Cyanobacteria.

1. Cloning of psbA Promoter and Bar Gene Into the pUC19:

pUC19 was digested with Sma I and ligated to the Sma I-Fnu DII fragment of pTB8 (Sugita, M. and Sugiura, M. (1984) Mol. Gen. Genet. 195, 308–313) containing the psbA promoter of N. tabaccum chloroplasts, giving rise to pUC19–32K. This plasmid was cut with Bam HI and ligated to the Bam HI fragment of pGSFR280 (De Block et al, (1987) EMBO 6, 2513–2518) which contains the bar gene, generating pUC19–32KSFR.

2. Construction of pWP3210

Figure 17:
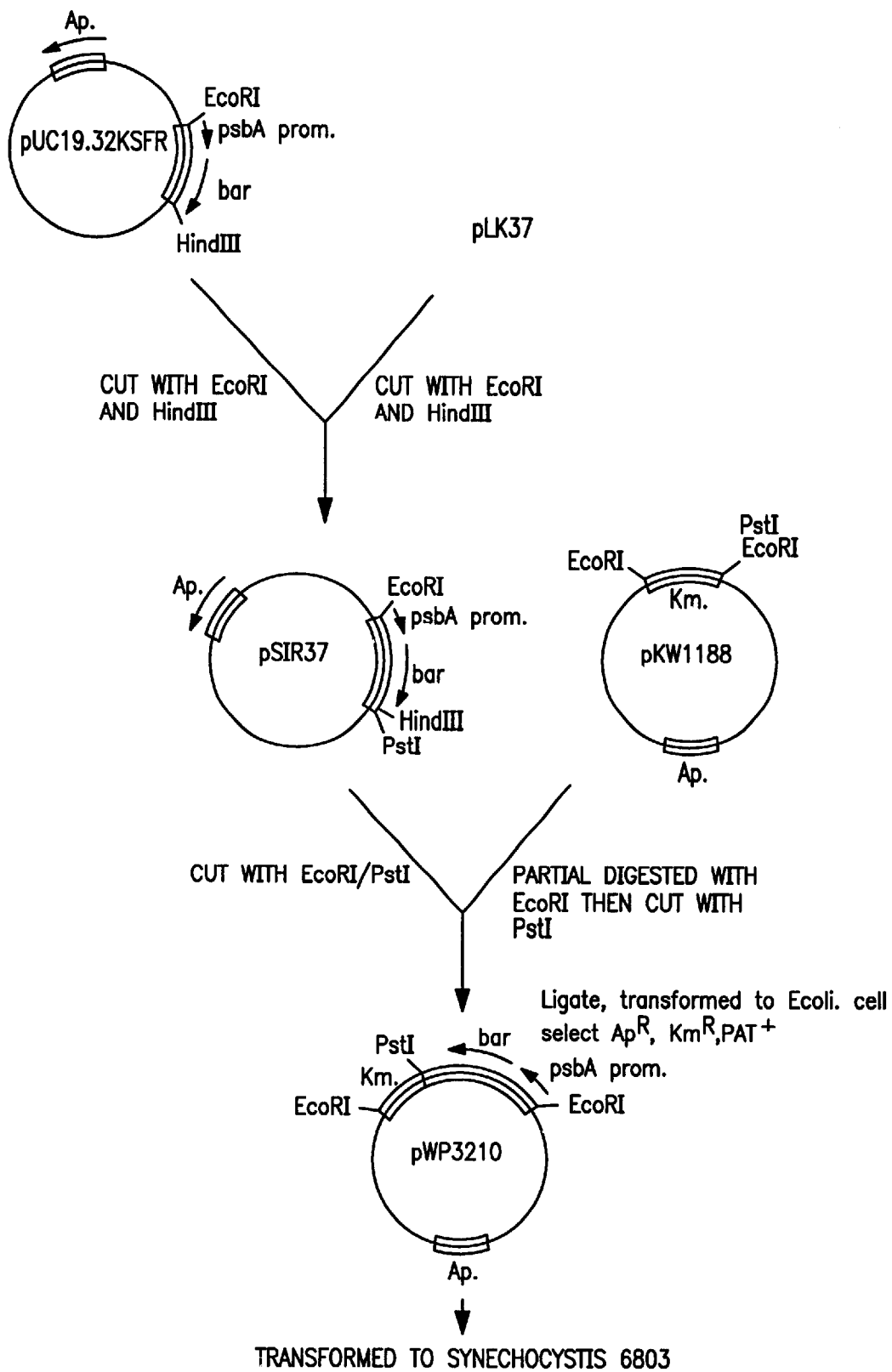
FIG. 17 shows the construction of pWP3210.

As outlined in FIG. 17, the pUC19–32KSFR was ligated to pLK37 (Botterman and Zabeau, (1988) DNA 6, 583–591), which is a vector containing polylinker cloning sites providing a Pst I site behind the Hind III site. The generated plasmid is called pSFR37. This pSFR37 is ligated to pKW1188 after digestion with Eco RI and PstI, resulting in pWP3210 containing Ampicillin, Kanamycin and Bialaphos resistance genes.

3. Transformation of Synechocystis with pWP3210

Synechocystis 6803 was transformed as described in Example 5. Transformants were selected on BG-11 medium containing 10 micrograms/ml Kanamycin and tested for the presence of bar gene as follows:

1) Detection of PAT-activity by TLC

Figure 18:
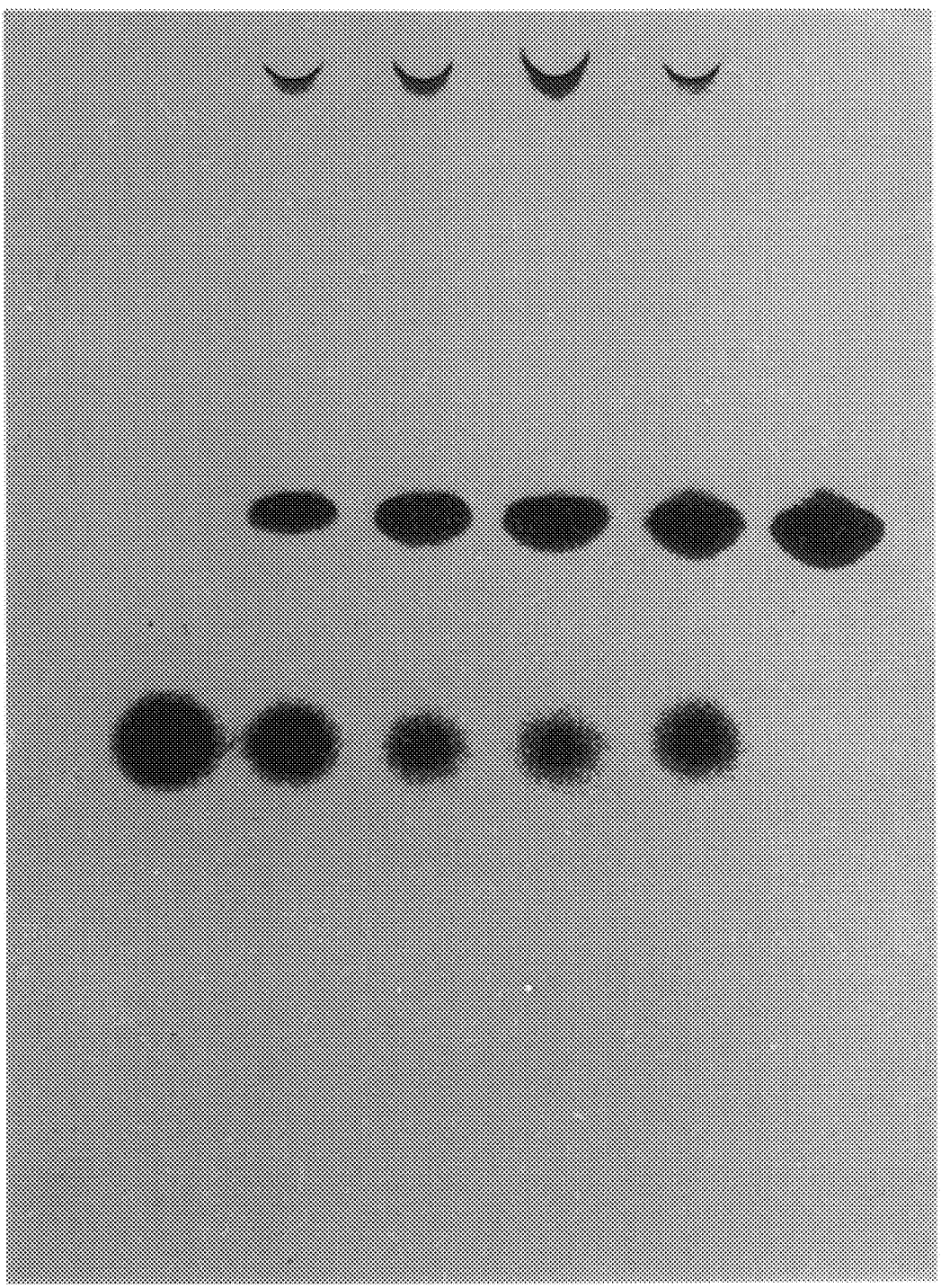
FIG. 18 shows detection of PAT activity by T.L.C. Lane 1 is an extract from Cyanobacterial transformed with vector pKW 1188; lane 2, 3, 4, 5 are extracts from four Cyanobacterial transformed with pWP 3210; lane 6 is 400 g of purified PAT.

The method of detection was carried out essentially according to De Block, M., et al. (1987) EMBO 6, 2519–2523. FIG. 18 shows that extracts from Synechocystis 6803 harboring pWP 3210 had PAT-activity, while that harboring vector pKW1188 did not.

2) Western Blot Analysis

Figure 19:
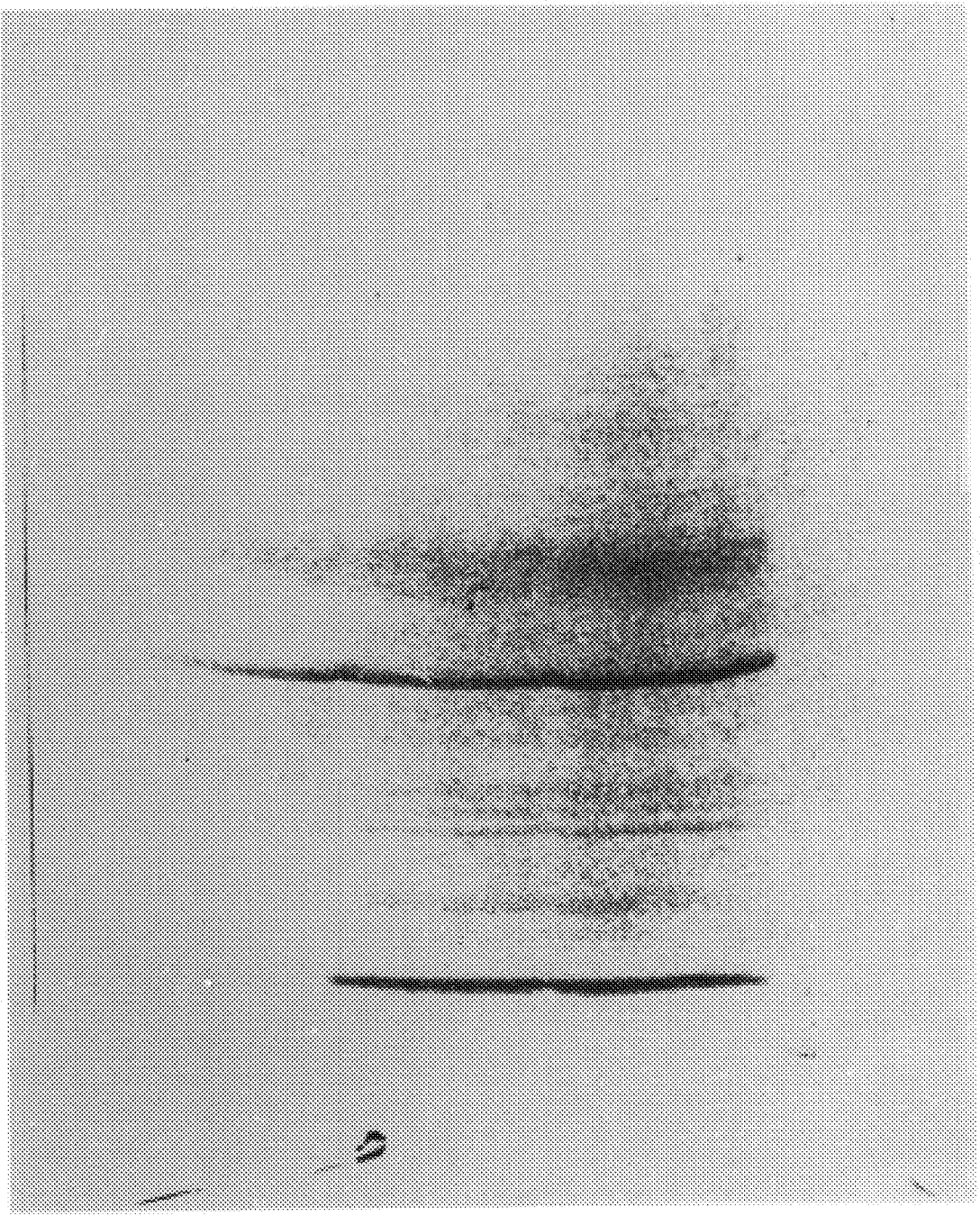
FIG. 19 shows detection of PAT protein by immunoblotting of Cyanobacterial extracts and treated with PAT antiserum. Lane 1 is an extract from Cyanobacterial transformed with vector pKW1188; lanes 2, 3 are extracts from Cyanobacterial transformed with pWP3210; lane 4 is purified PAT protein.

Analysis of crude Cyanobacterial extracts by Western blotting (FIG. 19) revealed the synthesis of a polypeptide of ±22KDa (lane 2,3). This gene product of ±22 KDa was confirmed that pWP 3210 coded for a fusion protein (14 amino acids from psbA structural gene and 183 amino acids from bar gene). This result also shows that the amount of PAT was about 0.2% of total soluble proteins in transformed Cyanobacteria.

3) Transformed Cyanobacterium is Resistant to PPT

Dilution of transformed Synechocystis 6803 was plated on BG-11 agar plate containing PPT (Table 4). The minimal inhibitory concentration (MIC) for Cyanobacteria transformed with pWP 3210 to PPT was>2000 micrograms/ml, while that transform with vector pKW 1188 was 25 micrograms/ml.

4) Simultaneous Expression of Bt8 and Bar Gene

According to Example 9, pKW1188 was partially digested with Bam HI and treated with Klenow polymerase. This digest was ligated to the Klenow treated EcoRI-Hind II fragment of pUC19–32KSFR containing the psbA promoter of *N. tabaccum* chloroplasts fused with the bar gene. The resulting plasmid is called pKW1188–4 and can be used for the transformation of Synechocystis.

TABLE 4

| PPT concentration ug/ml (in BG-11 agar plate) | # of Synechocystis 6803 transformed with | |
|---|---|---|
| | pKW 1188 colonies | pWP3210 colonies |
| 0 | 80 | 130 |
| 5 | 79 | 173 |
| 10 | 79 | 159 |
| 25 | 21 (very poor) | 141 |
| 50 | NG | 165 |
| 100 | NG | 130 |
| 500 | NG | 157 |
| 1000 | NG | 166 |
| 2000 | NG | 158 |

MIC for Synechocystis pKW 1188 to PPT–25 micrograms/ml MIC for Synechocystis pWP 3210 to PPT >2000 micrograms/ml. However, neither of these two transformants grow on Bialaphos at 5 micrograms/ml. This might be due to some materials in the Bialaphos preparation that inhibit the growth of Cyanobacteria.

EXAMPLE 12

Expression of Other Mosquitocidal Toxins in Cyanobacteria

Using the same strategy as described in Examples 9 and 10, the 3680 bp NDA-fragment or its truncated form of the Bt8 gene contained in pKW1188 can be replaced by other Bt genes, providing they encode mosquitocidal protein toxins. The list given below has to be considered as non-exhaustive and the genes cited as examples.

(1) the 3542 bp fragment encoding another 135 kDa mosquitocidal toxin from B.t. *israelensis* described by Ward and Ellar (1987) Nucl. Acids Res. 15, 141.

(2) the 3.6 kb XbaI fragment encoding another 130 kDa mosquitocidal toxin from B.t. *israelensis* described by Sekar and Carlton (1985) Gene 33, 151–158.

(3) the 4.3 kb BalI-EcoRI fragment encoding a 75 kDa mosquitocidal toxin from B.t. *israelensis* described by Thorne et al (1986) J. Bacterio. 166, 801–811.

(4) the 1680 bp fragment encoding the *B. sphaericus* mosquitocidal toxin described by Berrey and Hindley, (1987) Nucl. Acids Res. 15, 5891.

(5) the fragment encoding the P2 mosquitocidal toxin of B.t. *kurstaki* described by Donovan et al (1986) J. Biol. Chem. 263, 561–567.

(6) the 65 kDa toxin of strain B.t. *israelensis*, and its 34 kDa active fragment described by Witt et al. (186) European patent application nr. 0216 481 AZ.

EXAMPLE 13

The Use of Other Cyanobacteria to Express Mosquito Toxins

The genus Synechocystis is widespread in the environment and its ability to be easily transformed make it an ideal model for expression of mosquito toxin genes. However, there are many other Cyanobacteria which might be ingested by mosquitos and dominate some special environmental niches, for example rice paddies. Examples of the genera of these Cyanobacteria are non-exhaustively listed below:

Synechococcus

Aphjanothece

Gloeothece

Gloeocapsa

Anabaena

Agmenellum

Nostoc

Aphanizomenon

Chlorogloeopsis

Microcystis

Oscillatoria

Phormidium

Pseudanabaena

The following strain has been deposited in the Deutsche Sammlung von Mikroorganismen under the Budapest Treaty: *E. coli* MC 1061 harboring the plasmid pRFB 1188 (DSM 4430) *E. coli* K12 Hl trp harboring the plasmid pBIN10 (DSM 4020). PBIK 1188 (FIG. 6) has been deposited as IVI 10129 and PBTI 1188 (FIG. 7) has been deposited as IVI 10130 on Mar. 4, 1987 under the Budapest Treaty with In Vitro International, Inc., 611 Hammonds Ferry Road, Linthicum, Md. 21090.

It is intended that the foregoing description be only illustrative of the present invention and that the invention be limited only by the hereinafter appended claims.

What is claimed is:

1. A chimeric gene which is expressed in cells of a Cyanobacterium which is Synechocystis 6803 comprising:
   a) a DNA fragment comprising a promoter region which is effective for expression of a DNA fragment in the Cyanobacterium; and
   b) at least one DNA fragment coding for an insecticidally active protein endotoxin produced by a *Bacillus thuringiensis, Bacillus sphaericus* or *Bacillus kurstaki* strain, or for an insecticidally active truncated form of the above protein.

2. The chimeric gene of claim 1 containing an additional chimeric gene which is expressed simultaneously in the cells of the Cyanobacterium with the DNA fragment coding for the insecticidally active protein which comprises:

a DNA fragment coding for a bar gene protein which inactivates glutamine synthetase inhibitors.

3. The chimeric gene of claim 1 wherein the DNA fragment b) codes for wherein the endotoxin is produced by *Bacillus thuringiensis* var. *israelensis.*

4. The chimeric gene of claim 1 wherein the DNA fragment b) codes for the Bt8 protein of FIG. 2*b*.

5. The chimeric gene of claim 1 wherein the DNA fragment b) codes at least for the protein corresponding to the 774 amino-acid of the N-terminal extremity of the protein of FIG. 2*b*.

6. The chimeric gene of claim 1 wherein two DNA fragments (b) code for different endotoxins 27 kDa and 65 kDa in size.

7. The chimeric gene of claim 1 wherein the promoter region is lambdaPL.

8. The chimeric gene of claim 1 wherein the promoter region is a fragment of DNA comprising the sequence directing expression of the Cyanobacterium rubisco operon.

9. The chimeric gene of claim 1 wherein the promoter region is the promoter of the psbA gene of Synechocystis.

10. The chimeric gene of claim 1 wherein the promoter region is the promoter of the psbA gene or *Nicotiana tabaccum.*

11. A hybrid plasmid vector containing at least one chimeric gene which is expressed in cells of a cyanobacterium which is Synechocystis 6803 comprising:

(a) a DNA fragment comprising a promoter region which is effective for expression of a DNA fragment in the Cyanobacterium; and (b) at least one DNA fragment coding for an insecticidally active protein endotoxin produced by a *Bacillus thuringiensis, Bacillus sphaericus* or *Bacillus kurstaki* strain, or for an insecticidally active truncated form of the above protein.

12. The chimeric gene of claim 11 containing an additional chimeric gene which is expressed simultaneously as cells of the Cyanobacterium which comprises:

a DNA fragment coding for a bar gene protein which inactivates a glutamine synthetase inhibitor.

13. The hybrid plasmid vector of claim 11 wherein the DNA fragment b) codes for the Bt8 protein of FIG. 2*b*.

14. The hybrid plasmid vector of claim 11 wherein the DNA fragment b) codes at least for the protein corresponding to the 774 amino-acid of the N-terminal extremity of the protein of FIG. 2*b*.

15. The hybrid plasmid vector of claim 11 wherein the DNA fragment (a) is the lambdaPL promoter.

16. The hybrid plasmid vector of claim 11 wherein the DNA fragment (a) comprises the sequence directing expression of the Cyanobacterium rubisco operon.

17. The hybrid plasmid vector of claim 11 wherein the DNA fragment (a) is the promoter from the psbA gene either from Synechocystis or *Nicotiana tabaccum.*

18. The hybrid plasmid vector of claim 11 containing to DNA fragments b) coding for active proteins 27 kDa and 65 kDa in size.

19. A hybrid plasmid vector of claim 11 comprising an origin of replication of a bacterial plasmid.

20. A bacterial strain harboring the hybrid plasmid of claim 19.

21. A Cyanobacterium which is Synechocystis 6803 which contains at least one chimeric gene comprising:

(a) a DNA fragment comprising a promoter region which is effective for expression of a DNA fragment in the Cyanobacterium; and (b) at least one DNA fragment coding for an insecticidally active protein endotoxin produced by a *Bacillus thuringiensis, Bacillus sphaericus* or *Bacillus kurstaki* strain, or for an insecticidally active truncated form of the above protein.

22. The Cyanobacterium of claim 21 containing an additional chimeric gene which is expressed simultaneously in the cells of the Cyanobacterium which comprises:

a DNA fragment coding for a bar gene protein which inactivates a glutamine synthetase inhibitor.

23. The Cyanobacterium of claim 21 in which said chimeric gene is integrated into its chromosomal genome and is expressed.

24. The Cyanobacterium of claim 21 in which said chimeric gene is integrated into its chromosomal genome and is expressed and wherein the DNA fragment b) codes for the Bt8 protein of FIG. 2*b*.

25. The Cyanobacterium of claim 21 in which said chimeric gene is integrated into its chromosomal genome and is expressed and wherein the DNA fragment b) codes at least for a protein corresponding to the 774 amino-acid of the N-terminal extremity of the protein of FIG. 2*b*.

26.The Cyanobacterium of claim 219 in which said chimeric gene is integrated into its chromosomal genome and is expressed and wherein two DNA fragments b) code for different active endotoxin proteins 27 kDa and 65 kDa in size.

27. The Cyanobacterium of claim 21 in which said chimeric gene is integrated into its chromosomal genome and are expressed and wherein the DNA fragment (a) is the lambdaPL promoter.

28. The Cyanobacterium of claim 21 in which said chimeric gene is integrated into its chromosomal genome and is expressed and wherein the DNA fragment (a) is a fragment of DNA comprising the sequence directing expressing of the Cyanobacterium rubisco operon.

29. The Cyanobacterium of claim 21 in which said chimeric gene is integrated into its chromosomal genome and is expressed and wherein the DNA fragment is the promoter from the psbA gene from Synechocystis or *N. tabaccum.*

30. The Cyanobacterium of claim 22 in which said chimeric genes are integrated into its chromosomal genome and expressed and which is treated with glutamine synthetase inhibitors.

31. The Cyanobacterium of claim 30 wherein the glutamine synthetase inhibitor is selected from the group consisting of Bialaphos and Phosphinotricine.

32. A method of controlling mosquitos in water which comprises applying to a region to be controlled an insect controlling amount of the Cyanobacterium of claim 22 in which said chimeric genes are integrated into its chromosomal genome and are expressed.

33. A method of controlling mosquitos in water according to claim 32 in which said Cyanobacteria containing and expressing the bar gene are selectively protected against competing non-transformed Cyanobacteria by treating said region with glutamine synthetase inhibitors.

34. The method of claim 33 wherein the glutamine synthetase inhibitor is selected from the group consisting of Bialaphos and Phosphinotricine.

35. An insecticidal composition containing as active ingredient an insect controlling amount of the Cyanobacterium of claim 21 of in which said chimeric gene or said chimeric genes are integrated into its chromosomal genome and are expressed and their progeny.

36. The insecticidal composition of claim 35 containing the Cyanobacterium and their progeny and a carrier.

37. A plasmid having the identifying characteristics of plasmid TBIK 1188 or TBTI 1188 harbored within an *E. coli* deposited as IVI 10129 or IVI 10130, respectively.

38. A plasmid having the identifying characteristics of plasmid pBIN10 harbored within *E. coli* K12ΔH1Δtrp deposited as DSM 4020.

39. A plasmid having the identifying characteristics of plasmid pRFB1188 harbored with *E. coli* MC1062 deposited as DSM 4430.

40. A chimeric gene which is expressed in cells of a Cyanobacterium which is Synechocystis 6803 comprising:

(a) a DNA fragment comprising a promoter region which is effective for expression of a DNA fragment in the Cyanobacterium; and (b) a DNA fragment coding for a bar gene protein which inactivates glutamine synthetase inhibitors.

* * * * *

UNITED STATES PATENT AND TRADEMARK OFFICE
CERTIFICATE OF CORRECTION

PATENT NO.     : 6,335,008 B1
DATED          : January 1, 2002
INVENTOR(S)    : Mark Albert Vaeck, Wipa Chungjatupornchai and Lee McIntosh It is certified that error appears in the above-identified patent and that said Letters Patent is hereby corrected as shown below:

<u>Title page,</u>
Item [63], Related U.S. Application Data, "filed on Sep. 13, 1998, now abandoned", should be -- filed on Sept. 13, 1988, now abandoned --.

<u>Column 6,</u>
Line 50, "*Aedes aegyptiI*", should be -- *Aedes aegypti* --.

<u>Column 13,</u>
Line 56, "1.1383" should be -- 1.p1383 --.

<u>Column 14,</u>
Table 3, line 8, complete line should be moved to the right one column.

<u>Column 20,</u>
Line 37, "of Claim 219" should be -- of Claim 21 --.

<u>Column 21,</u>
Line 11, "of" after "Claim 21" should be deleted.

Signed and Sealed this

Twenty-first Day of January, 2003

JAMES E. ROGAN
*Director of the United States Patent and Trademark Office*